United States Patent
Kipp et al.

(10) Patent No.: US 8,491,792 B2
(45) Date of Patent: *Jul. 23, 2013

(54) NON-DISPERSIVE PROCESS FOR INSOLUBLE OIL RECOVERY FROM AQUEOUS SLURRIES

(75) Inventors: Peter B. Kipp, Houston, TX (US); Frank Seibert, Austin, TX (US); Rhykka Connelly, Austin, TX (US)

(73) Assignees: Board of Regents, The University of Texas System, Austin, TX (US); Organic Fuels Algae Technologies, LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/358,897

(22) Filed: Jan. 26, 2012

(65) Prior Publication Data

US 2012/0184759 A1  Jul. 19, 2012

Related U.S. Application Data

(63) Continuation-in-part of application No. 13/006,342, filed on Jan. 13, 2011, and a continuation-in-part of application No. 13/280,028, filed on Oct. 24, 2011.

(60) Provisional application No. 61/295,607, filed on Jan. 15, 2010.

(51) Int. Cl.
*B01D 11/00* (2006.01)
*B01D 61/00* (2006.01)
*B01D 15/04* (2006.01)
*C07C 57/00* (2006.01)

(52) U.S. Cl.
USPC .......... 210/644; 210/634; 210/638; 426/425; 554/1

(58) Field of Classification Search
USPC .. 210/234, 238, 644, 651, 634, 638; 426/425; 435/271, 134; 554/1
See application file for complete search history.

(56) References Cited

U.S. PATENT DOCUMENTS

| | | | |
|---|---|---|---|
| 3,956,112 A | 5/1976 | Lee et al. | |
| 4,439,629 A | 3/1984 | Ruegg | |
| 4,966,707 A | 10/1990 | Cussler et al. | |
| 5,078,886 A * | 1/1992 | Hsu | 210/632 |
| 5,167,824 A * | 12/1992 | Cohen et al. | 210/638 |
| 5,236,474 A * | 8/1993 | Schofield et al. | 95/47 |

(Continued)

FOREIGN PATENT DOCUMENTS

| | | |
|---|---|---|
| CA | 2248280 A1 | 10/1998 |
| JP | 2007-209955 | 8/2007 |
| WO | 2005/100542 A2 | 10/2005 |
| WO | 2011/088242 | 7/2011 |

OTHER PUBLICATIONS

International Search Report and Written Opinion for PCT/US2001/021185, dated Apr. 8, 2011, 21 pages.

(Continued)

*Primary Examiner* — Ana Fortuna
(74) *Attorney, Agent, or Firm* — Edwin S. Flores; Chalker Flores, LLP

(57) ABSTRACT

The development and application of a novel non-polar oil recovery process utilizing a non-dispersive solvent extraction method to coalesce and recover oil from a lysed or non-lysed Yeast slurry using a microporous hollow fiber (MHF) membrane contactor.

27 Claims, 14 Drawing Sheets

U.S. PATENT DOCUMENTS

| | | | | |
|---|---|---|---|---|
| 5,252,220 A | | 10/1993 | Coughlin et al. | |
| 5,378,369 A | * | 1/1995 | Rose et al. | 210/637 |
| 5,397,369 A | * | 3/1995 | Ohishi | 51/295 |
| 5,951,875 A | | 9/1999 | Kanel et al. | |
| 5,954,858 A | | 9/1999 | Peretti et al. | |
| 5,989,431 A | | 11/1999 | Evans et al. | |
| 6,146,535 A | | 11/2000 | Sutherland | |
| 6,436,290 B1 | | 8/2002 | Glassford | |
| 6,471,869 B1 | | 10/2002 | Yanou et al. | |
| 7,186,344 B2 | | 3/2007 | Hughes | |
| 8,110,112 B2 | | 2/2012 | Alburty et al. | |
| 8,128,827 B2 | | 3/2012 | Gallo et al. | |
| 8,202,425 B2 | * | 6/2012 | Kale | 210/634 |
| 2003/0185956 A1 | * | 10/2003 | Gradley | 426/534 |
| 2005/0098504 A1 | | 5/2005 | Manz et al. | |
| 2006/0191838 A1 | | 8/2006 | Lowell | |
| 2006/0275533 A1 | * | 12/2006 | Fletcher et al. | 426/491 |
| 2008/0083671 A1 | * | 4/2008 | Bomberger et al. | 210/643 |
| 2008/0156191 A1 | * | 7/2008 | Parekh et al. | 95/211 |
| 2009/0325269 A1 | | 12/2009 | Marschke | |
| 2010/0151098 A1 | * | 6/2010 | Catchpole et al. | 426/425 |
| 2010/0173806 A1 | | 7/2010 | Fan et al. | |
| 2011/0045528 A1 | | 2/2011 | Dhamwichukorn | |
| 2011/0065940 A1 | * | 3/2011 | Kahelin et al. | 554/1 |
| 2011/0138682 A1 | | 6/2011 | Demaris et al. | |
| 2011/0167712 A1 | | 7/2011 | Brasil | |
| 2011/0174734 A1 | * | 7/2011 | Seibert et al. | 210/650 |
| 2011/0192792 A1 | * | 8/2011 | Chew et al. | 210/633 |
| 2011/0225878 A1 | | 9/2011 | Moulijn et al. | |
| 2012/0077255 A1 | * | 3/2012 | Miranda et al. | 435/271 |
| 2012/0094340 A1 | * | 4/2012 | Morgan | 435/134 |
| 2012/0159839 A1 | * | 6/2012 | Koskinen et al. | 44/307 |
| 2012/0184759 A1 | * | 7/2012 | Kipp et al. | 554/175 |
| 2012/0208247 A1 | | 8/2012 | Kipp et al. | |
| 2012/0226061 A1 | | 9/2012 | Shepherd | |

OTHER PUBLICATIONS

PCT International Preliminary Report on Patentability for PCT/US2011/021185 dated Jul. 17, 2012, 13 pp.

* cited by examiner

FIG. 12A
FIG. 12B
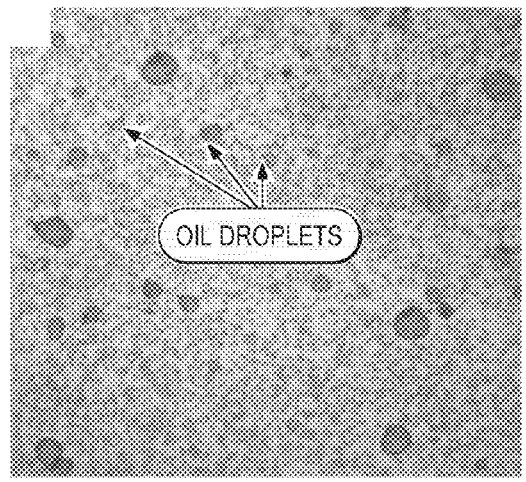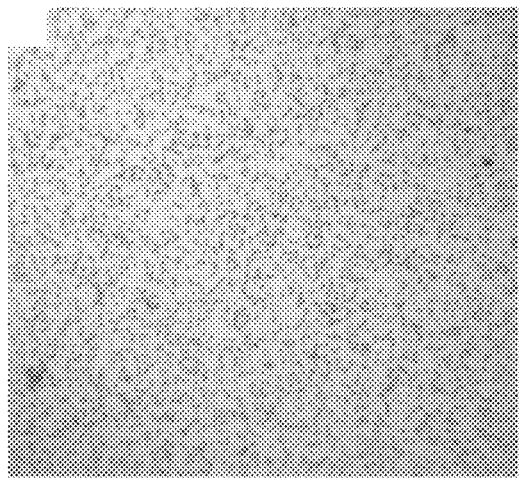
FIG. 13
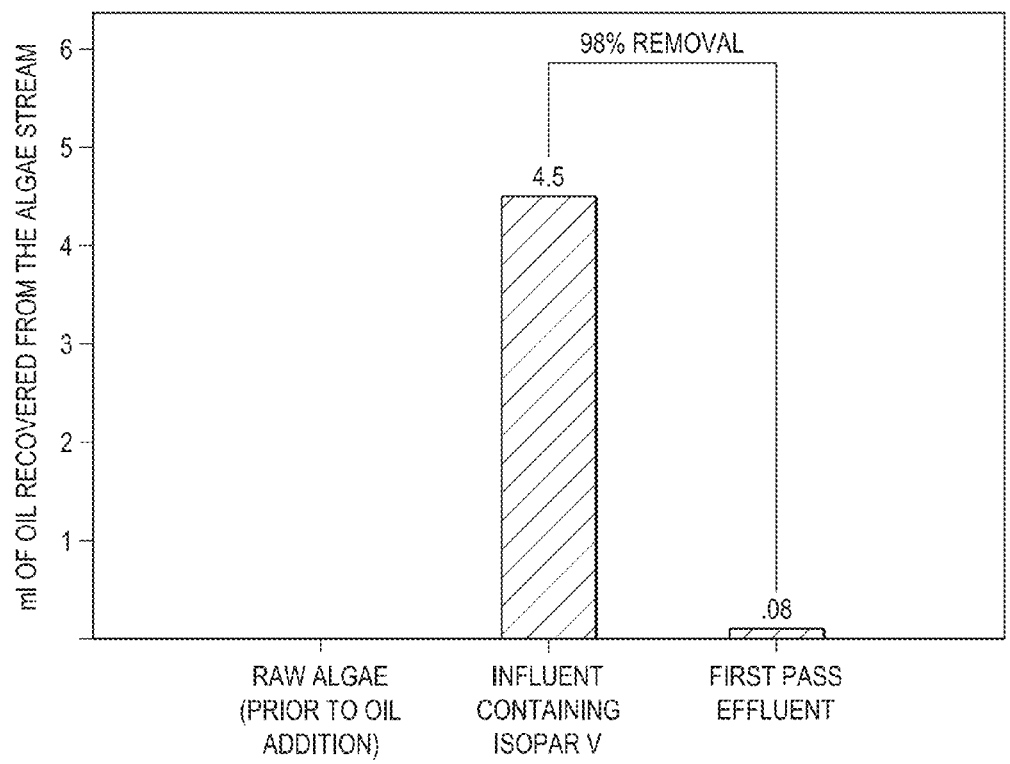

FIRST PASS

FIRST PASS

NON-DISPERSIVE PROCESS FOR INSOLUBLE OIL RECOVERY FROM AQUEOUS SLURRIES

CROSS-REFERENCE TO RELATED APPLICATIONS

This application claims priority to U.S. Provisional Application Ser. No. 61/295,607, filed Jan. 15, 2010, and is a Continuation-in-Part Application of U.S. patent application Ser. Nos. 13/006,342 filed Jan. 13, 2011 and 13/280,028 filed Oct. 24, 2011, the entire contents of each of which are incorporated herein by reference.

TECHNICAL FIELD OF THE INVENTION

The present invention relates in general to the field of insoluble oil recovery from aqueous slurries, and more particularly, to a microporous membrane based method for recovering oil from a growth media comprising lysed or non-lysed yeast cells capable of producing oil or other hydrophobic compounds.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with recovery methods for insoluble and low solubility compounds having economic value from aqueous mixtures that may include one or more types of biological cells or cellular debris.

U.S. Pat. No. 4,439,629 issued Mar. 27, 1984 to Ruegg describes a process for extracting either or both beta-carotene or glycerine from algae containing these substances, especially from algae of the genera *Dunaliella*. According to the Ruegg patent either or both of beta-carotene or glycerine can be extracted from algae. If it is desired to extract beta-carotene, the algae are first treated with calcium hydroxide and then filtered. The residue from this filtration is treated with a beta-carotene solvent, which removes the beta-carotene from the residue and into the solvent. The beta-carotene can be recovered from the solvent by conventional means. If it is desired to extract glycerine, the filtrate from the treatment of the algae with calcium hydroxide is neutralized, concentrated and the residue from the solid is treated with a lower alkanol to remove glycerine from the residue.

U.S. Pat. No. 5,378,639 issued Jan. 3, 1995 to Rose et al. discloses a method for the solvent-extraction of β-carotene from an aqueous algal biomass suspension, whereby a vegetable oil which is immiscible with water is mixed with an aqueous biomass suspension, the biomass containing the β-carotene, to form a mixture of the organic phase and the aqueous suspension, whereby the β-carotene is caused to dissolve in the organic phase. This is followed by separation of the organic phase from the aqueous phase by passing the organic phase containing the dissolved β-carotene through a semi-permeable membrane to effect microfiltration or ultrafiltration of the organic phase. The membrane is of a material that is hydrophobic and the organic phase is passed through the membrane with a pressure drop across the membrane which is lower than that which causes the aqueous phase to pass through the membrane.

SUMMARY OF THE INVENTION

In one embodiment, the present invention includes a method of extracting one or more insoluble oils from a liquid source, comprising Yeast, using one or more non-dispersive membrane contactors, by pumping the liquid source having the one or more oils from a reactor to the contactor; pumping a collection fluid through the one or more contactors; contacting the one or more oils in the liquid source with the collection fluid pumped in the one or more contactors; pumping a first stream from the contactor back to the reactor, wherein the first stream comprises the liquid source with the Yeast without extracted oils and the Yeast remain viable; and removing a second stream from the contactor or the vessel, wherein the second stream comprises the collection fluid and extracted oils. In one aspect, the reactor is a fermenter, and the Yeast are capable of secreting oil.

In one embodiment, the present invention includes a method of extracting oils from a liquid source having Yeast cells. The Yeast cells can be intact Yeast cells or contain lysed Yeast cells and the liquid source is then processed to remove the oil. In addition the Yeast cells can be removed from the liquid source and the oil can then be recovered. The Yeast cells may be separated from the liquid source by a number of methods including filtration, centrifugationprecipitation, flocculate and other methods known in the art.

In one aspect, the Yeast are selected from *Cryptococcus curvatus*, *Cryptococcus terricolus*, *Lipomyces starkeyi*, *Lipomyces lipofer*, *Endomycopsis vernalis*, *Rhodotorula glutinis*, *Rhodotorula gracilis*, *Candida* 107, *Saccharomyces paradoxus*, *Saccharomyces mikatae*, *Saccharomyces bayanus*, *Saccharomyces cerevisiae*, any *Cryptococcus*, *C. neoformans*, *C. bogoriensis*, *Yarrowia lipolytica*, *Apiotrichum curvatum*, *T. bombicola*, *T. apicola*, *T. petrophilum*, *C. tropicalis*, *C. lipolytica*, and *Candida* sp. The Yeast causes accumulation of one or more oils outside living cells. In another aspect, the method further comprises contacting the Yeast with chemical probes, exogenous agents, or pharmaceuticals, whereby the metabolism of the Yeast is modified and causes accumulation of the one or more oils outside living cells. In another aspect, the step of contacting the one or more oils in the liquid source with the collection fluid does not inhibit Yeast growth or viability of the organisms. In another aspect, the coalescence is achieved in the presence of Yeast cells.

In yet another aspect, the liquid source is selected from the group consisting of industrial water, brine, wastewater, industrial or natural effluents, water-oil mixtures, aqueous slurries, aqueous slurries comprising broken cells, live cells, biocellular mixtures, lysed cellular preparations, or combinations thereof. In another aspect, 95-100% of the one or more insoluble oils in the liquid source are extracted. In another aspect, the 45%, 50%, 55%, 60%, 65%, 70%, 75%, 80%, 85%, 90%, 95%, 98%, 99% and 100% of the one or more insoluble oils in the liquid source are extracted. In another aspect, the collection fluid comprises one or more solvents, a biodiesel, an oil, a non-polar oil or mixtures, or combinations thereof.

In another embodiment, the present invention includes a method of extracting one or more insoluble oils or hydrophobic components from a growth media comprising Yeast and the insoluble oils using one or more hydrophobic membranes or membrane modules comprising the steps of: pumping the growth media comprising the Yeast and insoluble oils from a reactor into a contactor or a vessel; pumping one or more collection fluids through the one or more membranes or membrane modules, wherein the one or more collection fluids counterflow with the growth media comprising Yeast in the contactor or the vessel; contacting the growth media comprising Yeast and insoluble oils in the contactor or the vessel with one or more collection fluids pumped through the one or more membranes or membrane modules; removing a first stream from the contactor or the vessel, wherein the first stream comprises the growth media and organism, wherein the Yeast can continue to produce the compound of interest; and removing a second stream from the contactor or the vessel, wherein the second stream comprises the one or more collection fluids and the one or more insoluble oils.

In one aspect, the method further comprises feeding or pumping the first stream to the reactor. In another aspect, the hydrophobic hollow fiber membrane is selected from at least one of polyethylene, polypropylene, polyolefins, polyvinyl chloride (PVC), amorphous Polyethylene terephthalate (PET), polyolefin copolymers, poly(etheretherketone) type polymers, or surface modified polymers. In another aspect, the counterflowing collection fluid comprises non-polar solvents, alkanes such as hexane, aromatic solvents such as benzene, toluene, ethers such as diethyl ether, halogenated solvents such as chloroform, dichloromethane, and esters such as ethyl acetate. In another aspect, the counterflowing collection fluid comprises non-polar oils, algal oils, components of biodiesels, monoglycerides, diglycerides, triglycerides, or fatty acid methyl esters.

In another aspect, the reactor is a fermenter, and the Yeast are capable of secreting one or more insoluble oils. In another aspect, the Yeast causes accumulation of one or more insoluble oils outside living cells. In another aspect, the method further comprises contacting the Yeast with chemical probes, exogenous agents, or pharmaceuticals, whereby the metabolism of the Yeast is modified and causes accumulation of the one or more insoluble oils outside living cells. In another aspect, the method includes the step of contacting the growth media comprising Yeast in the contactor or the vessel with one or more collection fluids pumped through the one or more membranes or membrane modules does not affect viability of the Yeast and/or the Yeast can continue to produce insoluble oils. In another aspect, the coalescence is achieved in the presence of the Yeast. In another aspect, the Yeast is genetically modified to render them capable of secreting hydrophobic components, Yeast that are capable of causing accumulation of the one or more hydrophobic components outside living cells, Yeast that are capable of causing accumulation of the one or more hydrophobic components outside living cells upon induction with one or more chemical probes, exogenous agents, or pharmaceuticals, or combinations thereof. In another aspect, at least 45%, 50%, 55%, 60%, 65%, 70%, 75%, 80%, 85%, 90%, 95%, 98%, 99% or 100% of the one or more hydrophobic components in the growth media are extracted. In another aspect, the collection fluid comprises one or more solvents, a biodiesel, an algal oil, a non-polar oil or mixtures, the oil secreted by the organism, or combinations thereof.

The present invention also describes a method for recovering insoluble oil from aqueous slurries using a hydrophobic microporous hollow fiber membrane followed by circulation of a collection fluid through the membrane. The collection fluid as described herein comprises an appropriate solvent for the insoluble or low solubility compound to be recovered, for e.g. heptane or a biodiesel mixture or the extracted oil or combinations thereof. The extracted oil can be used as the collection fluid for the recovery of additional oil, allowing the process to be conducted without a chemical solvent such as heptane. The novel process could be used in a wide variety of commercially significant applications such as: (i) recovery of released or secreted algae oil from an aqueous mixture, (ii) recovery of insoluble hydrocarbon and hydrocarbon-rich molecules from aqueous mixtures, (iii) recovery of Omega fatty acids from an aqueous mixture, (iv) recovery of Beta-carotene from an aqueous mixture, and (v) removal of oil from produced water in petroleum exploration and production.

BRIEF DESCRIPTION OF THE DRAWINGS

For a more complete understanding of the features and advantages of the present invention, reference is now made to the detailed description of the invention along with the accompanying figures and in which:

FIG. 12 shows the creation, visualization, and separation of an experimental algae/water/ISOPAR™ V emulsion.

FIG. 13 demonstrates the removal of ISOPAR™ V with a single pass through the membrane.

DETAILED DESCRIPTION OF THE INVENTION

Figure 1:
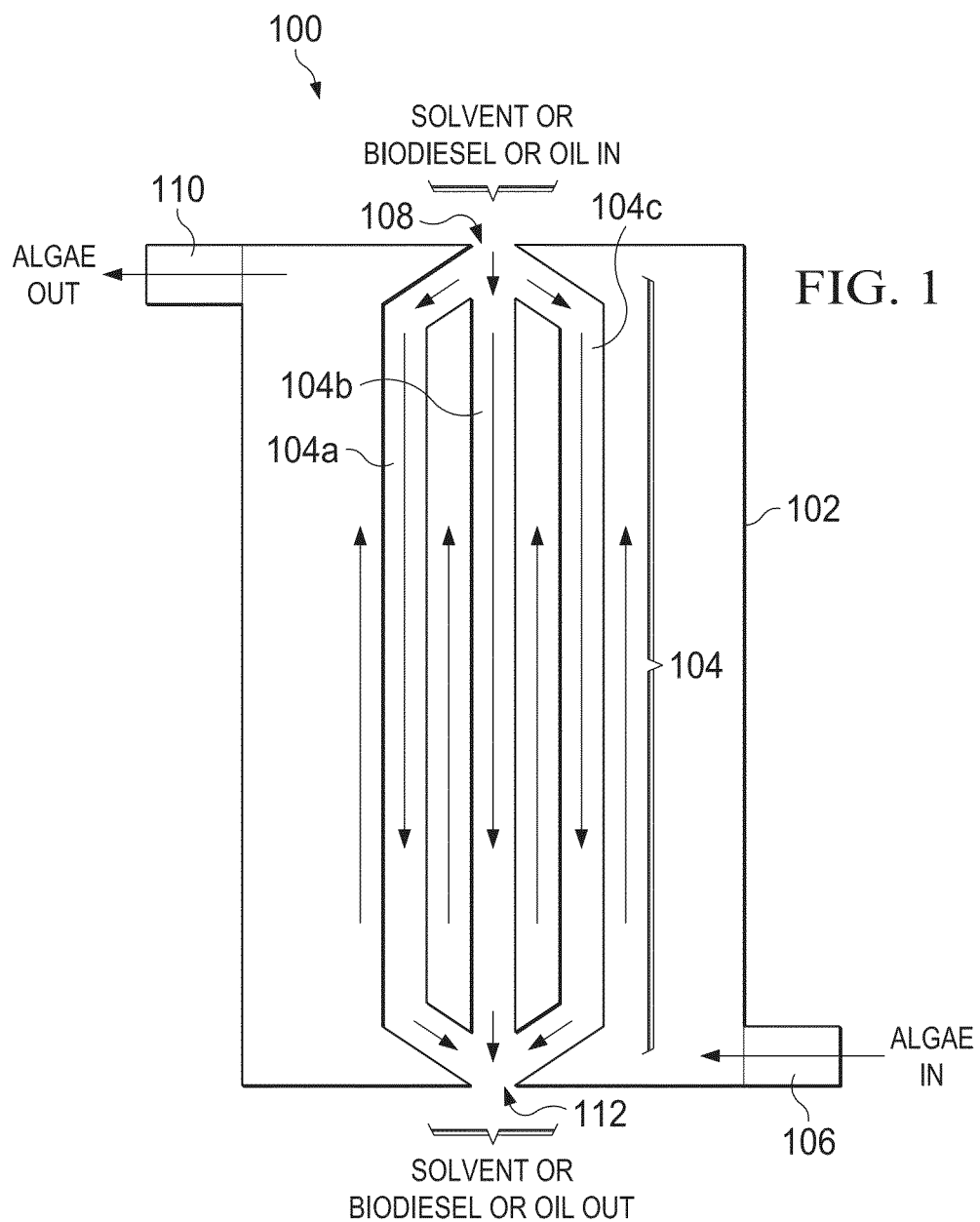
FIG. 1 is a schematic showing the method and the algal oil recovery principle as described in the embodiments of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "aqueous slurry" encompasses water based liquids containing any of the following in any combination; insoluble oils (hydrocarbons and hydrocarbon-rich molecules of commercial value), living, dead, damaged and/or broken cells (or not), proteins and other cellular debris, including sugars, DNA, RNA, etc. The slurry may also contain a solvent that was used to pre-treat cells to liberate compounds of interest.

The term "oil" as used herein refers to a single hydrocarbon or hydrocarbon-rich molecule including a complex mixture of lipids, hydrocarbons, free fatty acids, triglycerides, aldehydes, etc. The term oil also includes, e.g., $C_8$ (jet fuel compatible), $C_{60}$ (motor oil compatible) and oils that are odd- or even-chain oils (and mixtures thereof), e.g., from $C_6$ to $C_{120}$. Some compounds are pure hydrocarbons, some have oxygen, some will have phosphorus. Oil also comprises hydrophobic or lipophilic compounds.

The term "pumping" comprises all methods of pumping, propelling, or feeding fluid from one location to another employing hoses, lines, tubes ducts, pipes, or pipelines. It also includes gravity flow of fluid.

In conventional liquid-liquid extraction and coalescing processes involving large drops of oil (greater than 1,000 microns), the mixing and separation of the oil and water phases by a dispersive process is routinely practiced with relative ease. However, when the oil drops are significantly smaller in diameter (less than 10 microns) and solids are present, the complete separation of the immiscible liquids is extremely difficult, if not impossible using dispersive methods routinely practiced for larger oil droplets. When routine methods are applied to try to recover small oil droplets from water in the presence of solids (such as cells or cell debris), a solid-liquid-liquid emulsion layer is created resulting in an incomplete and inefficient separation of the two liquids. Therefore a new process is required that will allow for a more efficient separation and elimination of the solid-liquid-liquid-emulsion problem. The process of the present invention enables the recovery of micron and submicron sized insoluble oil drops from an aqueous slurry utilizing a novel non-dispersive process.

A non-dispersive process promotes a one-way flow of specific compounds into and through a membrane to remove the compounds from the shell side feed to the tube side. A non-dispersive separation process is currently used to remove dissolved gases from liquids such as the removal of dissolved oxygen from water to produce ultra pure water for the microelectronics industry. The present invention is a first successful demonstration of the application of non-dispersive processes to recover insoluble oil from water or aqueous slurries. The non-dispersive process disclosed herein uses a microporous hollow fiber membrane composed of hydrophobic fibers. The aqueous slurry containing the insoluble oil is fed on the shell-side of the hollow fiber module and a hydrocarbon-appropriate solvent, for example, a biodiesel, or similar oil recovered in previous application of the described process is fed on the tube side of the hollow fiber module as a collection fluid. The aqueous phase passes around the outside of the large surface area of hydrophobic fibers containing the hydrophobic collection fluid as it passes through and eventually out of the module. As the aqueous liquid with the insoluble oil drops passes through the module, the insoluble oil droplets coalesce on to the walls of the hydrophobic fibers and dissolve into the hydrocarbon-appropriate collection fluid on the tube side of the module and are carried out of the module with the collection fluid. In this process, the tube side collection fluid does not make prolonged contact with the aqueous phase or disperse into the aqueous phase. The absence of this mixing as hypothesized by the inventors prevents the formation of a solid-liquid-liquid emulsion, when solids were present, allowing insoluble oil to be recovered efficiently from an aqueous slurry containing solids. The above hypothesis was successfully demonstrated herein to efficiently recover insoluble oil from an aqueous mixture including cells without the formation of a solid-liquid-liquid emulsion.

In typical membrane filtration processes, small amounts of solids quickly build up on the surface of the membrane (commonly called membrane fouling) reducing the efficiency and cost effectiveness of the filtration process. In the process discovered and disclosed herein using the microporous hollow fiber membrane module, membrane fouling is not a concern within specific operating parameters. The present invention shows that if the module is operated using hydrophilic cells that are small enough to pass through the dimensions of the module, and an appropriate pressure differential is maintained between the aqueous fluid and collection fluid, then the hydrophilic cells flow through the module and are repelled from the surface of the membrane because the membrane is coated with a hydrophobic collection fluid. The results presented herein at the prescribed operating conditions do not indicate any evidence of membrane fouling.

The novel extraction process of the present invention utilizes a non-dispersive solvent extraction method to coalesce and recover an insoluble oil from an aqueous slurry. The technique utilizes a microporous hollow fiber membrane contactor. The inventors have tested the Liqui-Cel Extra Flow Contactor, commercially used for gas/liquid contacting, to obtain >80% extraction efficiency and process concentrates up to 10% bio-cellular solids without membrane fouling. The novel technique of the present invention utilizes the large coalescing area provided by the surface of the microporous hollow fibers when filled with a hydrophobic collection fluid and minimizes the actual contact of the solvent with the (e.g. Yeast) biomass and aqueous phase.

The novel extraction process described herein can be coupled with a variety of appropriate collection fluids for recovery of insoluble compounds, depending upon the types of compound or compounds to be recovered. The choice of collection fluid will impact both the sub-set of compounds recovered from the aqueous slurry as well as the downstream steps needed to economically and efficiently use compounds from the collection fluid. Differential extraction of desired molecules, for example, recovery of non-polar oils, but not polar oils, can be achieved by choice of collection fluid. Segregation of non-polar oils from polar oils, specifically polar oils containing phosphorous (e.g., phospholipids), is highly advantageous as phosphorus containing compounds complicate both the refining and transesterification processes used to create transportation fuels. Polar oils could be recovered using the process described herein using a different collection fluid, for example as a secondary recovery step once non-polar oils are already removed.

Downstream steps needed to recover desired molecules from the collection fluid are also application specific. If heptane is used as the collection fluid, compounds of interest may be recovered by distillation without the need of a steam stripper. If biodiesel (Fatty Acid Methyl Ester [FAME]) is used as the collection fluid, e.g., recovered oils may not require processing prior to transesterification to FAME. Importantly, the present invention can also use a "self" oil that has been previously extracted from an aqueous slurry as the collection fluid thereby completely eliminating the need and expense of having to separate the recovered compounds from the collection fluid. In this application, the collection fluid is a quantity of oil derived from a previously processed aqueous slurry or extracted by a different method. The microporous hollow fiber membrane contactor as described in the present invention is small, portable, economical and is capable of handling large aqueous slurry feed rates.

In one embodiment the present invention discloses a method of extracting one or more insoluble oils comprising lipid components, oils or both from an aqueous (lysed Yeast) preparation using one or more hydrophobic membranes or membrane modules. The method of the present invention comprises the following steps: (i) feeding an aqueous slurry comprising the insoluble oil by pumping in a contactor or a vessel, (ii) pumping one or more collection fluids through the one or more membranes or membrane modules. The one or more collection fluids counterflows with the aqueous slurry in the contactor or the vessel and comprise one or more solvents, a biodiesel, a non-polar oil extracted from process, or mixtures and combinations thereof, (iii) contacting the preparation in the contactor or the vessel with one or more collection fluids pumped through the one or more membranes or membrane modules, (iv) removing a first stream from the contactor or the vessel, wherein the first stream comprises the Yeast biomass, and (v) removing a second stream from the contactor or the vessel, wherein the second stream comprises the one or more collection fluids, one or more extracted, one or more oils or both.

In another embodiment, the present invention describes a method of extracting one or more hydrocarbons or hydrocarbon-rich molecules (e.g., farnesene, squalane, aldehydes, triglycerides, diglycerides, etc.) or combinations thereof, from an aqueous preparation using one or more hydrophobic membranes or membrane modules. Without limiting the scope of the invention, an example includes recovery of hydrocarbon and hydrocarbon-rich molecules produced by microbial fermentation. Microbial fermentation processes are described in which organisms including algae, yeast, *E. coli*, fungi, etc. are used to metabolize carbon sources (e.g., sugars, sugarcane bagasse, glycerol, etc.) into hydrocarbons and hydrocarbon-rich molecules that are secreted from (or accumulate within) the cells. Such organisms are expected, by design, to produce physically small oil droplets; the inventors hypothesized that these droplets will not readily resolve from water by gravity alone and that the process described herein will be immediately applicable to recover insoluble oils produced by microbial platforms. The companies commercializing microbial fermentation to oil technologies have implied that the recovery of the oil product is trivial, but emerging company disclosures and scientific data suggest recovering the oil from the aqueous growth media is a mission-critical problem. Technologies currently in use, for e.g. centrifugal force sufficient to pellet *E. coli* cells are not sufficient to break the oil/water emulsion that is created in the aqueous growth media by the hydrocarbon-producing *E. coli*.

In addition to the steps listed herein above the method of the present invention further involves the steps of collecting the one or more extracted algal lipid components, algal oils or both in a collection vessel, recycling the separated solvent by pumping through the one or more membranes or membrane modules to process a subsequent batch of lysed algae, converting the one or more extracted algal lipid components, algal oils or both in the collection vessel to Fatty Acid Methyl Esters (FAMEs) or a biodiesel by transesterification or alternatively, refinery-based processing such as hydrocracking or pyrolysis, and processing the first stream comprising the algal biomass by drying the algal biomass to be optionally used as animal feed, feedstock for chemical production, or for energy generation. In the event one or more solvents are used as the collection fluids, the method includes an optional step for separating the one or more extracted algal lipid components, algal oils or both from the one or more solvents. The lysed algal preparation used in the method of the present invention comprises a concentrate, a slurry, a suspension, a dispersion, an emulsion, a solution or any combinations thereof. In one aspect the hydrophobic membrane or membrane module comprises microporous hollow fiber membranes, selected from polyethylene, polypropylene, polyolefins, polyvinyl chloride (PVC), amorphous Polyethylene terephthalate (PET), polyolefin copolymers, poly(etheretherketone) type polymers, surface modified polymers, mixtures or combinations thereof. The surface modified polymers comprise polymers modified chemically at one or more halogen groups or by corona discharge or by ion embedding techniques. In another aspect of the method of the present invention the algae are selected from the group consisting of the diatoms (bacillariophytes), green algae (chlorophytes), blue-green algae (cyanophytes), golden-brown algae (chrysophytes), haptophytes, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochlorposis, Tetraselmis, Chlorella, Dunaliella, Oscillatoria, Synechococcus, Boekelovia, Isochysis* and *Pleurochysis*. In yet another aspect of the method of the present invention the one or more counterflowing solvents comprise non-polar solvents, alkanes such as hexane, aromatic solvents such as benzene, toluene, ethers such as diethyl ether, halogenated solvents such as chloroform, dichloromethane, and esters such as ethyl acetate. In one aspect the counterflowing non-polar oil comprises algal oils, components of biodiesels selected from monoglycerides, diglycerides, triglycerides, and fatty acid methyl esters.

The present invention also provides for a method of extracting one or more algal lipid components, algal oils or both from a lysed algal preparation using one or more hydrophobic membranes or membrane modules. In the first step the lysed algal preparation is fed to a contactor or a vessel by pumping while at the same time, pumping a solvent, biodiesel, an algal oil, a non-polar oil or mixtures thereof through the one or more membranes or membrane modules. The solvent, biodiesel, the algal oil, the non-polar oil or the mixture is pumped through the membrane such that it counterflows with the lysed algal preparation. Non-limiting examples of the non-polar oil used in the present invention includes non-polar algal oils, palm, canola, corn, etc. The one or more algal lipid components, algal oils or both coalesce on the surface of the membrane or the membrane module. The coalesced algal lipid components and the algal oils are removed from the surface of the membrane or the membrane module by contacting with the counterflowing solvent, biodiesel, the algal oil, the non-polar oil or the mixture. A first stream comprises an algal biomass is removed from the contactor or the vessel, followed by removal of a second stream comprising the counterflowing solvent, biodiesel, the algal oil, the non-polar oil or the mixture, one or more extracted algal lipid components, one or more algal oils or both. The method of extracting the algal oils or lipids without using a solvent further comprises the steps of: (i) collecting the one or more extracted algal lipid components, algal oils or both in a collection vessel, (ii) recycling the counterflowing oil by pumping a part or a whole of the contents of the collection vessel through the one or more membranes or membrane modules to process a subsequent batch of lysed algae, (iii) converting the one or more extracted algal lipid components, algal oils or both in the collection vessel to Fatty Acid Methyl Esters (FAMEs) or a biodiesel by transesterification, or delivery of oil to a refinery for processing by hydrocracking or pyrolysis, and (iv) processing the first stream comprising the algal biomass by drying the algal biomass to be optionally used as animal feed, biochemical feedstock, or for energy generation. The method further comprises the optional step of adding one or more natural fatty acids or salts thereof to the lysed algal preparation to aid in lipid transfer to the collection stream.

In one aspect of the method of the present invention the one or more natural fatty acids are designated as [X]:[Y], wherein X represents the number of carbon atoms in the one or more fatty acids ranging from 8-22 and Y represents one or more double bonds in the fatty acids ranging from 0-6. In another aspect the one or more natural fatty acids or salts thereof comprise Myristoleic acid, Palmitoleic acid, Sapienic acid, Oleic acid, Linoleic acid, α-Linolenic acid, Arachidonic acid, Eicosapentaenoic acid, Erucic acid, Docosahexaenoic acid, Lauric acid, Myristic acid, Palmitic acid, Stearic acid, Arachidic acid, and combinations thereof. In yet another aspect the lysed algal preparation comprises a concentrate, a slurry, a suspension, a dispersion, an emulsion, a solution or any combinations thereof.

The counterflowing non-polar oil used in the present invention comprises algal oils, various components of biodiesels selected from monoglycerides, diglycerides, triglycerides, and fatty acid methyl esters. In a related aspect the hydrophobic membrane or membrane module comprises microporous hollow fiber membranes, selected from polyethylene, polypropylene, polyolefins, polyvinyl chloride (PVC), amorphous Polyethylene terephthalate (PET), polyolefin copolymers, poly(etheretherketone) type polymers, surface modified polymers, mixtures or combinations thereof. The surface modified polymers comprise polymers modified chemically at one or more halogen groups or by corona discharge or ion embedding techniques. In one aspect the algae are selected from the group consisting of the diatoms (bacillariophytes), green algae (chlorophytes), blue-green algae (cyanophytes), golden-brown algae (chrysophytes), haptophytes, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochlorposis, Tetraselmis, Chlorella, Dunaliella, Oscillatoria, Synechococcus, Boekelovia, Isochysis* and *Pleurochysis*.

In another embodiment the instant invention describes a contactor or vessel for extracting one or more insoluble oil components from the bio-cellular aqueous slurry such as but not limited to algal oils or both from a lysed algal concentrate. The contactor or vessel as described herein comprises, an external metallic, polypropylene or other polymeric casing, one or more microporous hollow fiber membrane cartridges comprising a plurality of microporous hollow fiber membranes enclosed by the metal casing, wherein the one or more membrane cartridges divide the casing into a shell-side and a fiber side, one or more baffles on the shell-side of the metal casing, one or more distribution tubes on the fiber-side of the metal casing, two inlet ports connected to the external metal casing, wherein the lysed algal concentrate is pumped to the shell-side through the first inlet port and a strip gas or a solvent is fed to the fiber side through the second inlet port, and two outlet ports connected to the metal casing, wherein the an algal raffinate comprising the algal biomass is removed from the first outlet port and a solvent/extracted lipid or oil mixture or the strip gas is removed from the second outlet port.

In one aspect the microporous hollow fiber membrane comprises polyethylene, polypropylene, polyolefins, polyvinyl chloride (PVC), amorphous Polyethylene terephthalate (PET), polyolefin copolymers, poly(etheretherketone) type polymers, surface modified polymers, mixtures or combinations thereof. The surface modified polymers comprise polymers modified chemically at one or more halogen groups or by corona discharge or ion embedding techniques. In another aspect the algae used for the extraction of the algal oil or lipids are selected from the group consisting of the diatoms (bacillariophytes), green algae (chlorophytes), blue-green algae (cyanophytes), golden-brown algae (chrysophytes), haptophytes, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochlorposis, Tetraselmis, Chlorella, Dunaliella, Oscillatoria, Synechococcus, Boekelovia, Isochysis* and *Pleurochysis*.

In yet another embodiment the present invention discloses a method of extracting one or more algal oils from a lysed algal concentrate in a contactor using one or more hydrophobic microporous hollow fiber membrane modules comprising a plurality of microporous hollow fiber membranes comprising the steps of: (i) pumping the lysed algal concentrate through a first inlet port of the contactor to a shell-side of the contactor, (ii) pumping one or more collection fluids through a second inlet port of the contactor to the one or more hollow fiber membranes on a fiber side of the contactor; wherein the one or more collection fluids counterflows with the lysed algal preparation on the shell-side of the contactor. The one or more collection fluids comprise one or more solvents, a biodiesel, an algal oil, a non-polar oil or mixtures thereof, (iii) contacting the lysed algal concentrate on the shell-side with the one or more non-polar solvents on the fiber side, (iv) removing a first stream from a first outlet port in the contactor, wherein the first stream comprises an algal biomass, and (v) removing a second stream from a second outlet port in the contactor, wherein the second stream comprises the collection fluid and the one or more extracted algal oils. The extraction method described in the embodiment of the present invention further comprises the steps of: (i) collecting the one or more extracted algal oils in a collection vessel, (ii) recycling the separated solvent by pumping through the one or more microporous hollow fiber membranes to process a subsequent batch of lysed algae, (iii) converting the one or more extracted algal oils in the collection vessel to Fatty Acid Methyl Esters (FAMEs) or a biodiesel by transesterification or conversion to fuels by refinery-based methods such as hydrocracking and pyrolysis, and (iv) processing the first stream comprising the algal biomass by drying the algal biomass to be optionally used as animal feed or for energy generation. In one aspect the extraction method as described herein comprises the optional step of separating the one or more extracted algal oils from the one or more solvents.

In another aspect the counterflowing solvents comprise non-polar solvents, alkanes such as hexane, and aromatic solvents such as benzene, toluene, and ethers such as diethyl ether, halogenated solvents such as chloroform, dichloromethane, and esters such as ethyl acetate. In yet another aspect 45-80% of the one or more algal oils in the lysed algal concentrate are extracted by the method of the present invention. As per the method described in the present invention 45%, 55%, 60%, 65%, 70%, 75%, and 80% of the one or more algal oils in the lysed algal concentrate are extracted.

The present invention further describes a method of extracting one or more algal oils from a lysed algal concentrate in a contactor using one or more hydrophobic microporous hollow fiber membrane modules comprising a plurality of microporous hollow fiber membranes. The first step of the method involves pumping a lysed algal concentrate through a first inlet port of the contactor to a shell-side of the contactor followed by pumping a solvent, biodiesel, an algal oil, a non-polar oil or mixtures thereof through a second inlet port of the contactor through the one or more membranes or membrane modules on a fiber side of the contactor. The biodiesel, the algal oil, the non-polar oil or the mixture is pumped through the membrane such that it counterflows with the lysed algal preparation on the shell-side of the contactor. The algal oils coalesce on the microporous hollow fiber membrane and are removed from the surface of the membrane by contacting with the counterflowing solvent, biodiesel, the algal oil, the non-polar oil or the mixture. A first stream comprising an algal biomass is removed from a first outlet port in the contactor followed by the removal of a second stream from a second outlet port in the contactor. The second stream comprises the counterflowing biodiesel, the algal oil, the non-polar oil or the mixture and the one or more extracted algal oils.

The algal oil extraction method as described in an embodiment of the present invention further comprises the steps of: collecting the one or more extracted algal oils in a collection vessel, recycling the counterflowing oil by pumping a part or a whole of the contents of the collection vessel through the one or more microporous hollow fiber membranes to process a subsequent batch of lysed algae, converting the one or more extracted algal oils in the collection vessel to Fatty Acid Methyl Esters (FAMEs) or a biodiesel by transesterification or conversion to fuels by refinery-based methods such as hydrocracking and pyrolysis, and processing the first stream comprising the algal biomass by drying the algal biomass to be optionally used as animal feed, biochemical feedstock, or for energy generation. In one aspect the method comprises the optional step of adding one or more natural fatty acids or salts thereof, hydrocarbon and hydrocarbon rich molecules, including aldehydes (flavors and fragrances), terpenes (chemical feedstocks), etc. to the lysed algal preparation. In another aspect the one or more natural fatty acids are designated as [X]:[Y], wherein X represents the number of carbon atoms in the one or more fatty acids ranging from 8-22 and Y represents one or more double bonds in the fatty acids ranging from 0-6. The one or more natural fatty acids (saturated or unsaturated) or salts thereof comprise Myristoleic acid, Palmitoleic acid, Sapienic acid, Oleic acid, Linoleic acid, α-Linolenic acid, Arachidonic acid, Eicosapentaenoic acid, Erucic acid, Docosahexaenoic acid, Lauric acid, Myristic acid, Palmitic acid, Stearic acid, Arachidic acid, and combinations thereof. In another aspect the counterflowing oil comprises non-polar oils, components of biodiesels selected from monoglycerides, diglycerides, triglycerides, and fatty acid methyl esters. In yet another aspect the hydrophobic hollow fiber membrane comprises polyethylene, polypropylene, polyolefins, polyvinyl chloride (PVC), amorphous Polyethylene terephthalate (PET), polyolefin copolymers, poly (etheretherketone) type polymers, surface modified polymers, mixtures or combinations thereof, wherein the polymers are modified chemically at one or more halogen groups or by corona discharge or ion embedding techniques.

Another embodiment of the present invention discloses a method of extracting one or more insoluble oils from a liquid source using one or more hydrophobic membranes or membrane modules comprising the steps of: (i) feeding the liquid source comprising the one or more insoluble oils by pumping in a contactor or a vessel, (ii) pumping one or more collection fluids through the one or more membranes or membrane modules, wherein the one or more collection fluids counterflows with the liquid source in the contactor or the vessel, wherein the one or more collection fluids comprise one or more solvents, a biodiesel, an algal oil, a non-polar oil or mixtures and combinations thereof, (iii) contacting the one or more insoluble oils in the liquid source in the contactor or the vessel with one or more collection fluids pumped through the one or more membranes or membrane modules, (iv) removing a first stream from the contactor or the vessel, wherein the first stream comprises the liquid source without the one or more insoluble oils, and (v) removing a second stream from the contactor or the vessel, wherein the second stream comprises the one or more collection fluids and the one or more extracted insoluble oils.

The extraction method as described above further comprises the steps of: collecting the one or more extracted insoluble oils in a collection vessel, recycling the separated solvent by pumping through the one or more membranes or membrane modules to process a subsequent batch of the liquid slurry, and converting the one or more extracted insoluble oils comprising algal lipid components, algal oils or both in the collection vessel to Fatty Acid Methyl Esters (FAMEs) or a biodiesel by transesterification or a refinery-based process such as hydrocracking or pyrolysis. The liquid source used in the method of the present invention is selected from the group consisting of industrial water, brine, wastewater, industrial or natural effluents, water-oil mixtures, aqueous slurries, aqueous slurries comprising broken cells, live cells or combinations thereof, bio-cellular mixtures, lysed cellular preparations, and combinations thereof. In one aspect of the method discloses hereinabove the biocellular mixture comprises algae, protists, fungi, yeast, $E.\ coli$, mixed cultures of cells, and combinations thereof. In another easpect the method extracts 45-100% of the one or more insoluble oils in the liquid source. In yet another aspect 45%, 50%, 55%, 60%, 65%, 70%, 75%, 80%, 85%, 90%, 95%, 98%, 99% and 100% of the one or more insoluble oils in the liquid source are extracted.

The present invention describes a method for recovering algae oil from lysed algae concentrate using hydrophobic microporous hollow fiber membrane followed by recovery of the algal oil using a collection fluid which can be a solvent, a biodiesel, an algal oil or mixtures thereof. The technique of the present invention does not require intimate contacting of the lysed algae concentrate and solvent. The use of a hydrophobic microporous hollow fiber membrane provides a non-dispersive method of coalescing and recovering the algal oil. The lysed algae concentrate is fed on the shell side while algal oil or the biodiesel mixture is fed on the fiber side. The algal oil acts to sweep and the remove the coalesced oil within the tube surface of the hollow fibers. A natural fatty acid maybe added to the algae concentrate to minimize fouling on the fiber outer surface and increase oil coalescence. A simple schematic representation of the method of the present invention is depicted in FIG. 1.

FIG. 1 shows an algal oil recovery unit 100. The unit 100 comprises a housing 102, within which is contained a membrane module 104 comprising a plurality of microporous hollow fiber membrane units depicted as 104a, 104b, and 104c. The unit has two inlet ports 106 and 108. The lysed algal preparation is fed (pumped) through port 106. A collection fluid is pumped through inlet port 108. The collection fluid can be a solvent, a biodiesel, an algal oil or mixtures thereof. The algal preparation counterflows with the collection fluid flowing inside the microporous hollow fiber membranes 104a, 104b, and 104c. The algal oils or lipid coalesce on the surface of the hollow fiber membranes and are swept by and recovered by the collection fluid. The algal preparation exits the unit 100 through the outlet port 110. The exit stream is taken for further processing (e.g. solvent recovery) if necessary. The collection fluid flows out of the unit 100 through port 112.

The method of the present invention using a biodiesel mixture as the collection fluid eliminates the need of a distillation system or a stripper to recover the solvent thereby reducing the capital and operating cost of the overall oil recovery process.

A wide variety of organisms can be used to generate oils and lipids that can be extracted with the present invention. Non-limiting examples of algae and microalgae may be grown and used with the present invention including one or more members of the following divisions: *Chlorophyta, Cyanophyta* (Cyanobacteria), and *Heterokontophyt*. Non-limiting examples of classes of microalgae that may be used with the present invention include: Bacillariophyceae, Eustigmatophyceae, and Chrysophyceae. Non-limiting examples of genera of microalgae used with the methods of the invention include: *Nannochloropsis, Chlorella, Dunaliella, Scenedesmus, Selenastrum, Oscillatoria, Phormidium, Spirulina, Amphora*, and *Ochromonas*. Non-limiting examples of microalgae species that can be used with the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*.

Other sources for biomass can be a wild type or genetically modified fungus. Non-limiting examples of fungi that may be used with the present invention include: *Mortierella, Mortierrla vinacea, Mortierella alpine, Pythium debaryanum, Mucor circinelloides, Aspergillus ochraceus, Aspergillus terreus, Penicillium iilacinum, Hensenulo, Chaetomium, Cladosporium, Malbranchea, Rhizopus*, and *Pythium*. As the source of biomass is not limited using the devices and methods of the present invention can be wild type or genetically modified yeast. Non-limiting examples of yeast that can be used with the present invention include *Cryptococcus curvatus, Cryptococcus terricolus, Lipomyces starkeyi, Lipomyces lipofer, Endomycopsis vernalis, Rhodotorula glutinis, Rhodotorula gracilis, Candida* 107, *Saccharomyces paradoxus, Saccharomyces mikatae, Saccharomyces bayanus, Saccharomyces cerevisiae*, any *Cryptococcus, C. neoformans, C. bogoriensis, Yarrowia lipolytica, Apiotrichum cur-*

*vatum, T. bombicola, T. apicola, T. petrophilum, C. tropicalis, C. lipolytica*, and *Candida* sp., e.g., *Candida albicans*.

The biomass can even be any bacteria that generate lipids, oils, proteins, and carbohydrates, whether naturally or by genetic engineering. Non-limiting examples of bacteria that can be used with the present invention include *Escherichia coli, Acinetobacter* sp. any actinomycete, *Mycobacterium tuberculosis*, any streptomycete, *Acinetobacter calcoaceticus, P. aeruginosa, Pseudomonas* sp., *R. erythropolis, N. erthopolis, Mycobacterium* sp., *B., U. zeae, U. maydis, B. lichenformis, S. marcescens, P. fluorescens, B. subtilis, B. brevis, B. polmyma, C. lepus, N. erthropolis, T. thiooxidans, D. polymorphis, P. aeruginosa* and *Rhodococcus opacus*.

There is no simple and economical method for extracting the oil directly from an aqueous slurry. Drying Yeast is usually needed for solvent extraction and the biomass is exposed to toxic solvents. Other methods such as supercritical extraction are uneconomical for commodity products such as fuel. Solvent extraction is somewhat promising but requires distillation of an extract to separate the solvent from the oil. Also, a steam stripper is usually required to recover the residual solvent dissolved or entrained within the exiting Yeast concentrate. The solvent extraction technique requires contactor equipment or phase separation equipment, a distillation system and a steam stripper along with varying heat exchangers, surge tanks and pumps. Also steam and cooling water are required. The process described herein only requires a membrane system with pumps and tanks. No steam or cooling water is required.

Processing Alternatives: After selection of the appropriate solvent, the next step is to determine whether to extract Yeast oil from "wet" or "dry" Yeast. The "dry" process requires dewatering and evaporating the water from the Yeast biomass and then lysing the Yeast. Lysing is a process of breaking the cell wall and opening the cell. Solvent may be contacted with the dry Yeast in special counter current leaching equipment. The solvent and extracted Yeast oil is separated in a vacuum distillation tower or evaporator. The remaining Yeast biomass with residual solvent is fed to a special evaporator to remove and recover the solvent and to dry the Yeast biomass again. The "dry" process suffers from having to dry the algae a second time when the solvent must be evaporated away, handling a high solids stream in multiple steps, and potentially leaving solvent in the residual Yeast solids.

The "wet" process requires lysing and extraction of the algae concentrate. The wet process requires an excellent lysing technique followed by a solvent extraction process, which provides adequate mass transfer area for dissolving/coalescing the non-polar lipids. The "wet" process offers the advantages of drying the Yeast only once and leaving less residual solvent in the Yeast biomass. To minimize the processing cost, the "wet" process appears to offer significant advantages.

The present invention focuses on the "wet" process and the novel non-dispersive extraction contactor used to coalesce and dissolve the desirable non-polar lipids.

Figure 2:
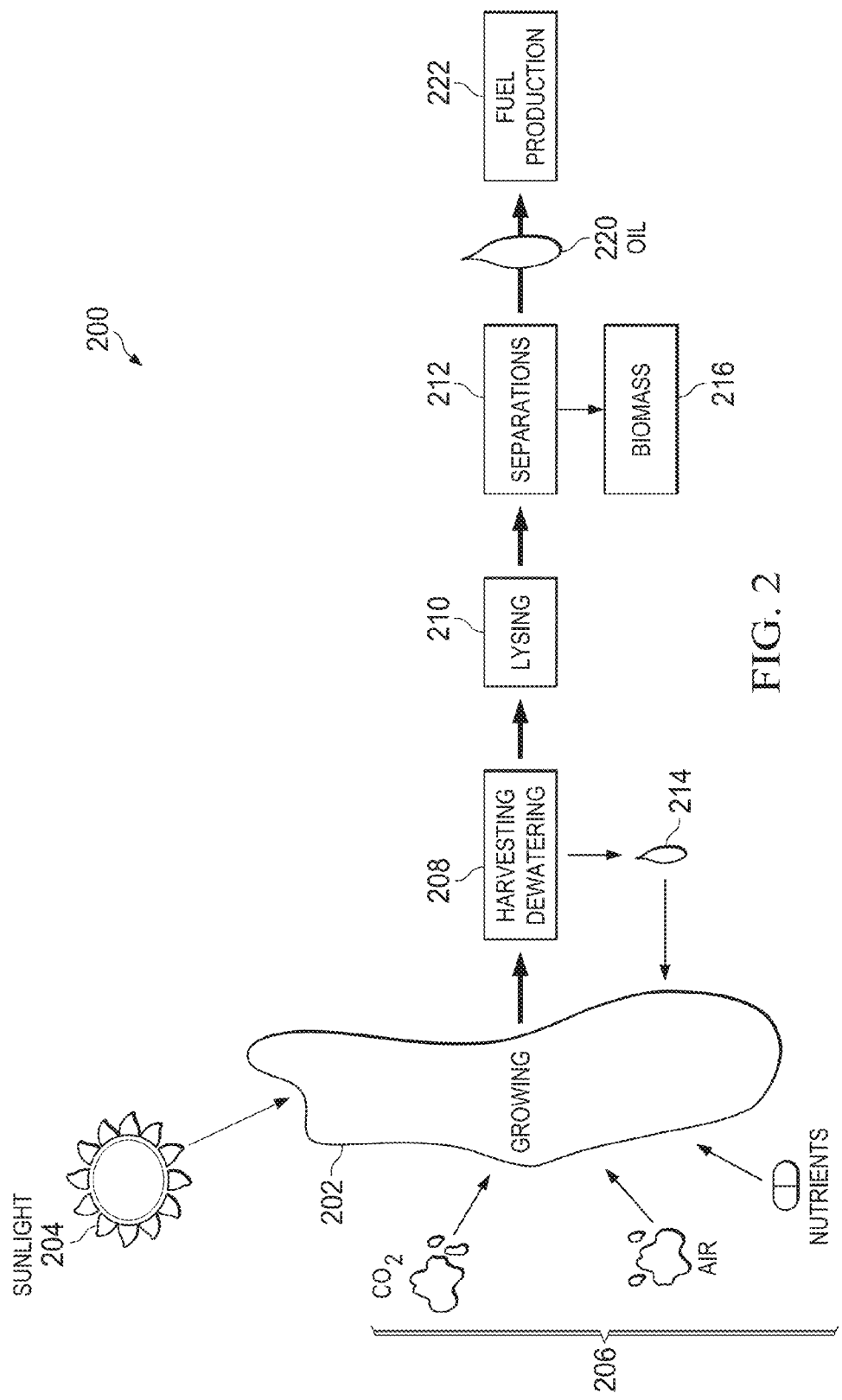
FIG. 2 is a schematic of a general algal oil production process.
Figure 3A:
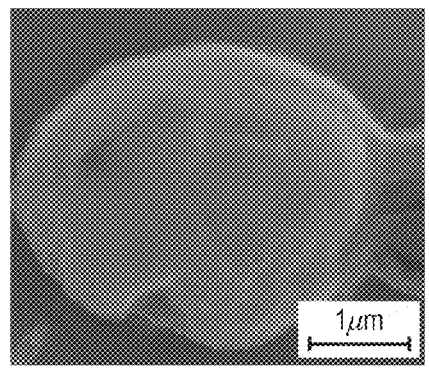
FIGS. 3A and 3B shows photographs of an alga cell prior to (3A) and after lysing (3B)
Figure 3B:
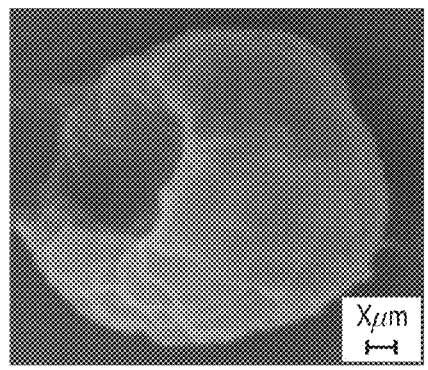
Figure 3C:
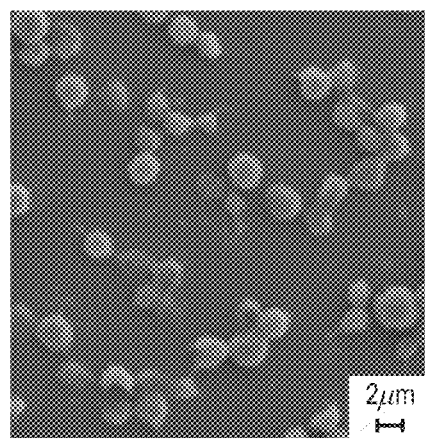
FIGS. 3C and 3D shows photographs of algal cells prior to (3C) and after lysing (3D)
Figure 3D:
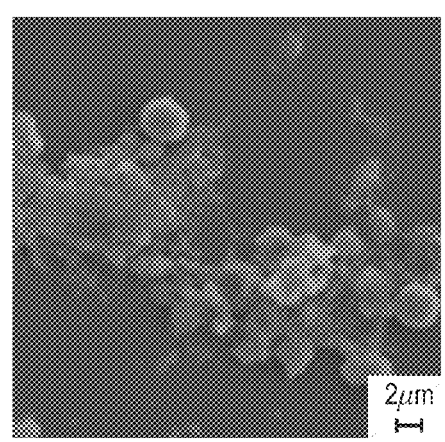

As shown in FIG. 2, the algal oil recovery method 200 begins by growing algae in a pond 202. Sunlight 204 and the elements 206 are provided to the algae in pond 202. The elements 206 comprise carbon dioxide ($CO_2$), air and nutrients for the algae. The oil extraction step 212 follows the algae concentration 208 and lysing 210 steps. After growing and initial harvesting, from the pond 202 the dilute algae feed is concentrated significantly. The typical algae concentration obtained from the pond 202 generally ranges from 100 to 300 mg dried algae/liter of solution. The goal of the concentration step 208 is to remove and recycle the water 214 back to the pond. Concentration methods 208 vary from centrifugation to flocculation/settling of the algae. To maximize lysing and extraction efficiency, it is important that concentrate being fed for lysing is not flocculated. After the concentration step 208, the algae concentrate is sent to the lysing 210 processing step where the algae cell is mechanically or electromechanically broken, thus exposing and freeing the non-polar oil. Various techniques may be used to mechanically or electrically compress and decompress to break the cell. In general after lysing, 212 the algae cell can be disintegrated or opened-up as shown in FIG. 3. FIGS. 3A and 3C shows photographs of an alga cell prior to lysing and FIGS. 3C and 3D show photographs of algal cells prior after lysing.

Once the oil has been freed from inside the Algae cell, the oil will not simply separate from the cellular biomass due to density differences. Also since the equivalent diameters of most microAlgae are extremely small and on the order of 1-5 microns, the oil drop diameter is often much less than 1 micron. Such oil drops do not rise or coalesce with other drops very well and can form a stable emulsion. When solid Algae biomass 216 is added to the mixture, the recovery of the oil is even more difficult. Therefore simple gravitational phase settling is not a viable oil separation option after lysing.

After lysing, the algae concentrate is fed to the separations step 212 where algae oil 220 is separated from the wet algal biomass 216. The algae oil 220 is then provided to a fuel production step 222. The biomass 216 may be sent for further drying and will be used for animal feed or processed further for energy generation applications.

Figure 4:
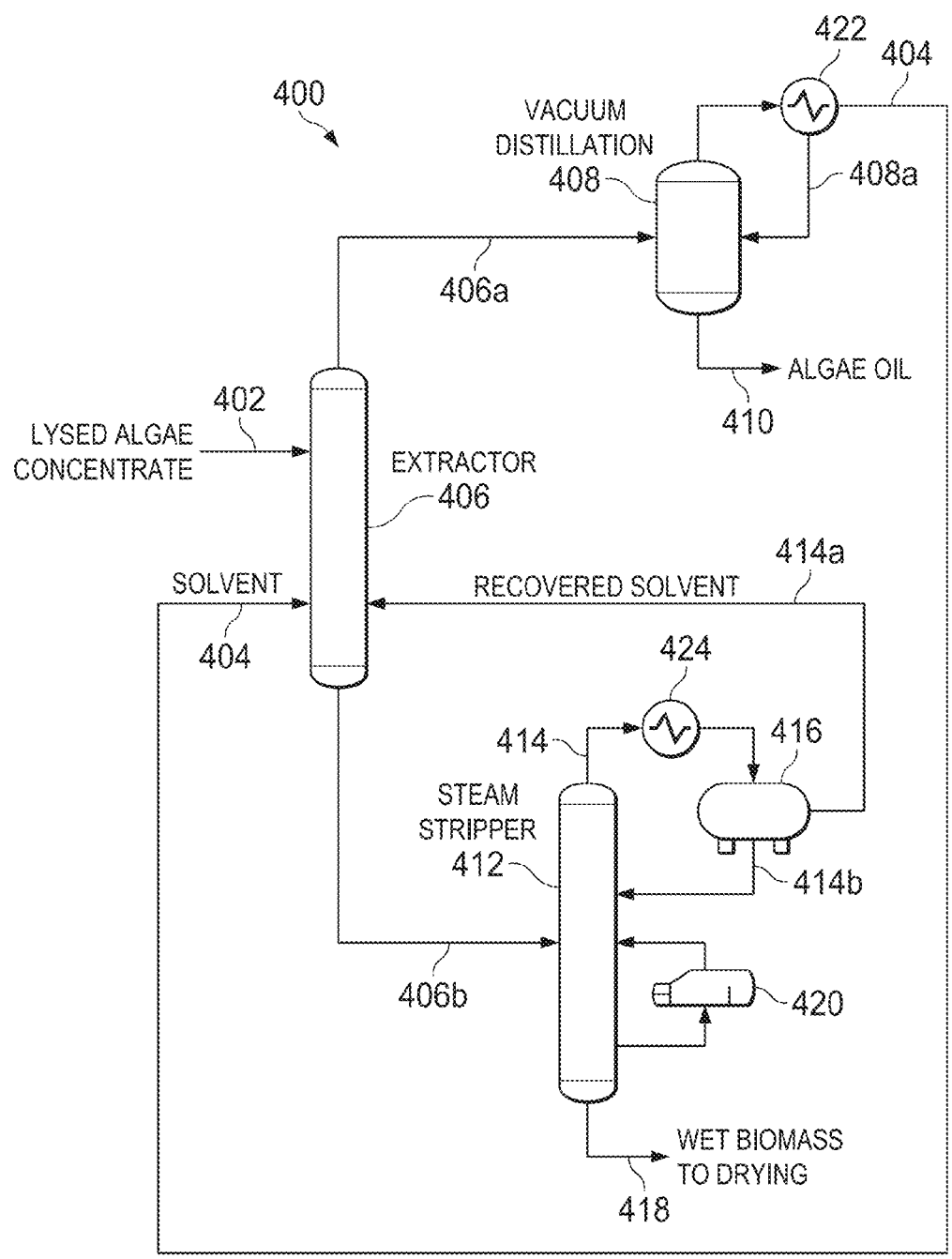
FIG. 4 is a flow diagram of a general algae oil extraction process.

As shown in FIG. 4, the typical solvent extraction process involves 1) an extraction step to recover Algae oil from the lysed biomass, 2) a vacuum distillation or evaporation step to separate the oil and solvent where the solvent is returned to step 1, and 3) if necessary, steam stripping step to recover the dissolved and entrained solvent leaving the extraction step with the Yeast or algal biomass.

FIG. 4 a flow diagram 400 of a general algae oil extraction process using a conventional dispersive extraction column 406. Lysed algal concentrate 402 and solvent 404 is fed to a column extractor 406 to extract the algal oils and lipids. Stream 406a comprises the solvent 404 containing the algal oils and lipids. Stream 406a is then fed to a vacuum distillation unit 408 to recover the solvent 404 and the algal oil 410. The separated solvent without any oil or other constituents 404 is fed back to the extractor 406. In the event it needs further purification (separation), the solvent 404 is fed back to the vacuum distillation unit 408 (via valve 422 and stream 408a). A second stream 406b from the extractor 406 comprises the algal biomass, solids, and residual solvent. Stream 406b is passed through a stream stripper 412, to separate the wet biomass 418 and other solids from the solvent 404. The wet biomass 418 is subjected to further drying. The recovered solvent 414 is collected in a decanting vessel 416 via valve 424 before being recycled back to the extractor 406 via stream 414a. A second stream 414b from the vessel 416 recycles any dissolved solvent in condensed steam 414 back to the stream stripper 412. A heater unit 420 heats a portion of the water condensate from the bottom of the steam stripper 412 and turns the water condensate back into steam and recycles the steam back into the steam stripper 412.

Extraction Processing and Equipment: The desired extraction process for Yeast oil recovery must satisfy certain requirements and avoid potential deficiencies for economic recovery. There are several "wet" extraction processes for oil recovery that are technically feasible but are not necessarily economical. Minimal oil recovery costs are critical if the ultimate use of the recovered Yeast oil is fuel.

The optimum oil extraction process should include: (i) processing a bio-cellular aqueous slurry containing oil, (ii) using a non-polar solvent or extracted oil with extremely low miscibility in water, (iii) using a solvent (if necessary), that easily separates from the oil, (iv) using an extraction equipment that can handle high processing feed rates and easily scaled-up, (v) using an extraction equipment that minimizes the entertainment of solvent into the biomass, (vi) using an extraction equipment that provides a high contact area for mass transfer and non-polar lipid coalescence, (vii) using an extraction equipment capable of handling concentrated Yeast feeds and not be irreversibly fouled by Yeast solids, (viii) using an extraction equipment that is relatively compact and potentially portable to allow transport to different Algae production sites, and (ix) using an extraction equipment that is readily available, inexpensive and safe.

Membrane based processes for separations have been in existence for a long time. There are many types of membranes. Most membrane processes however use porous membranes wherein the membrane material performs a separation as a result of differences in diffusion and equilibrium between chemical components and on the molecular level. The present inventors however utilize a microporous membrane, which is rarely used commercially except for applications involving the transfer of gases to or from a liquid such as water. The microporous membranes function very differently from the porous membrane because of their relatively large pores. The microporous membranes do not truly separate chemical components on the molecular level like porous membranes do. The present invention relies on the coalescence of non-polar lipids present within the Algae slurry to coalesce onto the hydrophobic surfaces provided by the hollow fibers. The vast surface area of the membrane, combined with the hydrophobic collection fluid's ability to wet the membrane, creates a surface capable of coalescing small lipid droplets. Once coalesced into the collection fluid, the lipids are transported out of the membrane through the inner tubes of the hollow fibers.

Membrane based Oil Recovery Process: For example, the application of a microporous hollow fiber (MHF) membrane contactor as the optimal extraction equipment appears ideally suited for the recovery of Algae oil. The MHF contactor provides all of the optimum characteristics listed previously. The application MHF contactor to Algae oil recovery is novel, minimizes solvent loss, eliminates need for the steam stripper, minimizes solids contamination, and is easy to operate. The process does not involve dispersing a solvent into the Algae biomass. The non-dispersive nature of the contactor is attractive in minimizing solvent loss and thus potentially eliminating the need for a steam stripper. A collection fluid typically comprising of either a solvent (such as hexane) or a biodiesel mixture, or Yeast or algal oil is circulated through the hollow fibers for the recovery of the Yeast or algal oils. The application of the MHF contactor in conjunction with a biodiesel mixture circulated through the microporous hollow fibers eliminates the need for a solvent and distillation column. The two oil extraction processing schemes with solvent and the biodiesel mixture are shown in FIGS. 5 and 6, respectively.

Figure 5:
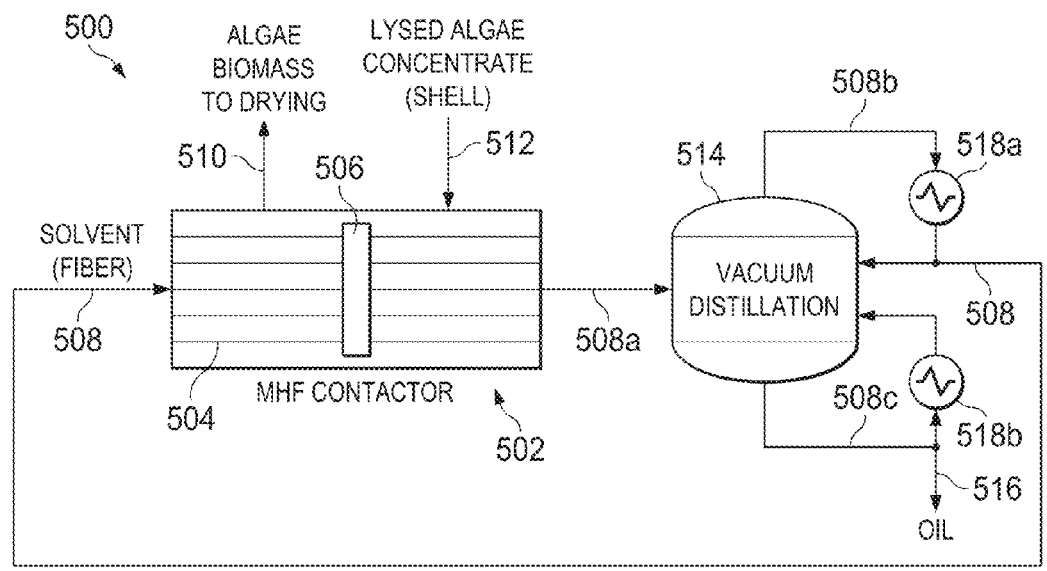
FIG. 5 is a flow diagram of the novel algal oil extraction process (with solvent) of the present invention.

FIG. 5 is a schematic 500 depicting the novel algal oil extraction process (with solvent 508 in a collection fluid) of the present invention. The process comprises a MHF contactor 502 comprising a plurality of microporous hollow fiber membranes 504 and a central baffle 506. Solvent 508 is fed (pumped) through the tube side of the membrane fibers 504 to wet the shell side surface of the membrane fibers 504 to contact the lysed algal concentrate 512 at the wetted shell side surface of the membrane fibers 504. The lysed algal concentrate 512 is contained in the shell portion of the MHF contactor 502. There are two exit streams from the contactor 502, an algal biomass stream 510 which is processed further (dried) and a solvent stream 508a which contains the extracted algal oils and lipids 516. The stream 508a is passed through a vacuum distillation unit 514 to separate the oil 516 from the solvent 508 and to recover the solvent 508 for recycle and reuse. Exit stream 508b from the distillation unit 514 comprises pure solvent 508 which is recycled via valve 518a and fed to the contactor 502 to repeat the process and solvent requiring further separation and is recycled back via valve 518a to the distillation unit 514. Exit stream 508c from the distillation unit 514 comprises the algal oils 516. A portion of this stream is vaporized (518b) and returned to the distillation unit 514.

Figure 6:
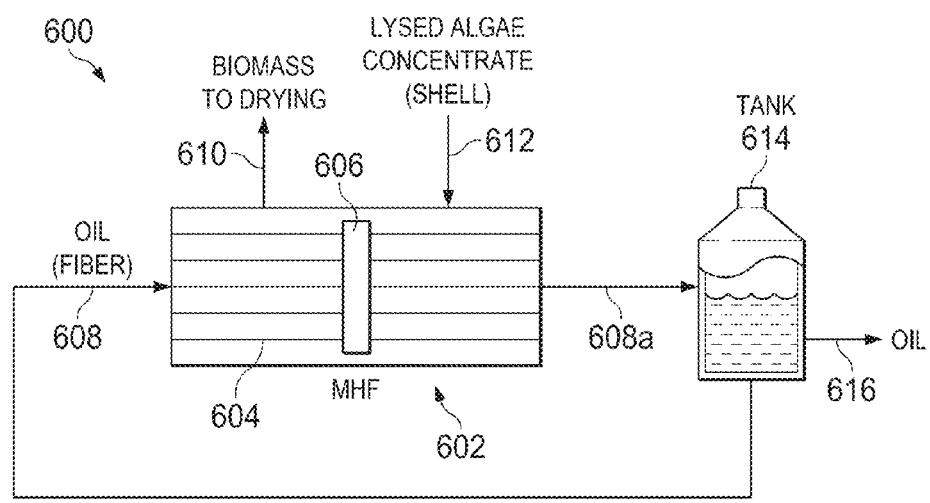
FIG. 6 is a flow diagram of the novel algal oil extraction process (without solvent) of the present invention.

FIG. 6 is a schematic 600 depicting the novel algal oil extraction process (without solvent in or as the collection fluid, using a non-polar algae oil mixture as the collection fluid) of the present invention. The process comprises a MHF contactor 602 comprising a plurality of microporous hollow fiber membranes 604 and a central baffle 606. Non-polar algae oil 608 is fed (pumped) through the tube side of the membrane fibers 604 to wet the shell side surface of the membrane fibers 604 and to contact the lysed algal concentrate 612 at the wetted shell side surface of the membrane fibers 604. The lysed algal concentrate 612 is contained in the shell portion of the MHF contactor 602. The non-polar algae oil 608 functions to dissolve and sweep the coalesced oil from the algae concentrate. The non-polar oil 608 coalesces onto the hydrophobic fiber surface 604 and dissolves into oil contained in the walls and the counterflowing oil phase 608 and can be removed. There are two exit streams from the contactor 602, an algal biomass stream 610 which is processed further (dried) and a stream 608a which contains the algal oils and lipids 616 that is collected in a tank 614. Part of the oil 616 can be removed from the tank 614 and fed to the contactor 602 to repeat the process.

Microporous hollow fiber contactors were initially developed in the 1980s. These early studies focused on lab-scale prototype modules containing just a few fibers. These early studies promoted the possibility of liquid-liquid extraction applications. The contacting of two immiscible liquids such as water and a non-polar solvent is unique with MHF contactors in that there is no dispersion of one liquid into another. This technology is sometimes referred to as non-dispersive extraction. The hollow fibers are generally composed of a hydrophobic material such as polyethylene or polypropylene. These hollow fibers could be made of a different material but it should be hydrophobic to avoid fouling of the fiber surface with the Algae solids which are usually hydrophilic. The solvent should be a hydrocarbon with a very low solubility in water and is pumped through the hollow fibers. As a result of the hydrophobicity of the fiber material, the solvent will wet the microporous fibers and fill the micropores. The aqueous-based fluid is pumped through the shell-side of the membrane contactor. To prevent breakthrough of the solvent into the shell-side, the shell or aqueous side is controlled at a higher pressure than the fiber or hydrocarbon side. This results in immobilizing a liquid-liquid interface in the porous walls of the hollow fibers. Unfortunately when these modules were scaled-up for liquid-liquid extraction, the performance was usually disappointingly poor. Further studies identified the poor efficiency was a result of shell-side bypassing. An improved version (referred to as the Liqui-Cel Extra Flow contactor) was developed which eliminated the possibility of shell-side bypassing by incorporating a shell-side distributor. While the design eliminated the shell-side bypassing, the new design eliminated true counter-current contacting. The overall performance was improved somewhat relative to the original design. Nevertheless, the new design did not correct the fundamental limitations of pore-side mass transfer resistance that would control most commercially significant extraction applications. As a result, only a few commercial liquid extraction applications using MHF contacting technology exist today.

Also, the MHF contactors often required expensive filter systems to avoid plugging with solids associated with most commercial liquid-liquid extraction processes. The Liqui-Cel contactor used in the present invention has been applied almost exclusively to commercial processes that transfer a gas to or from a liquid such as oxygen stripping from water for the microelectronics industry.

No applications of the MHF contactors are known for enhancing coalescence and removing of submicron oil drops from water. Certainly no applications of MHF technology are known for submicron oil recovery from water involving a significant solids concentration.

Figure 7:
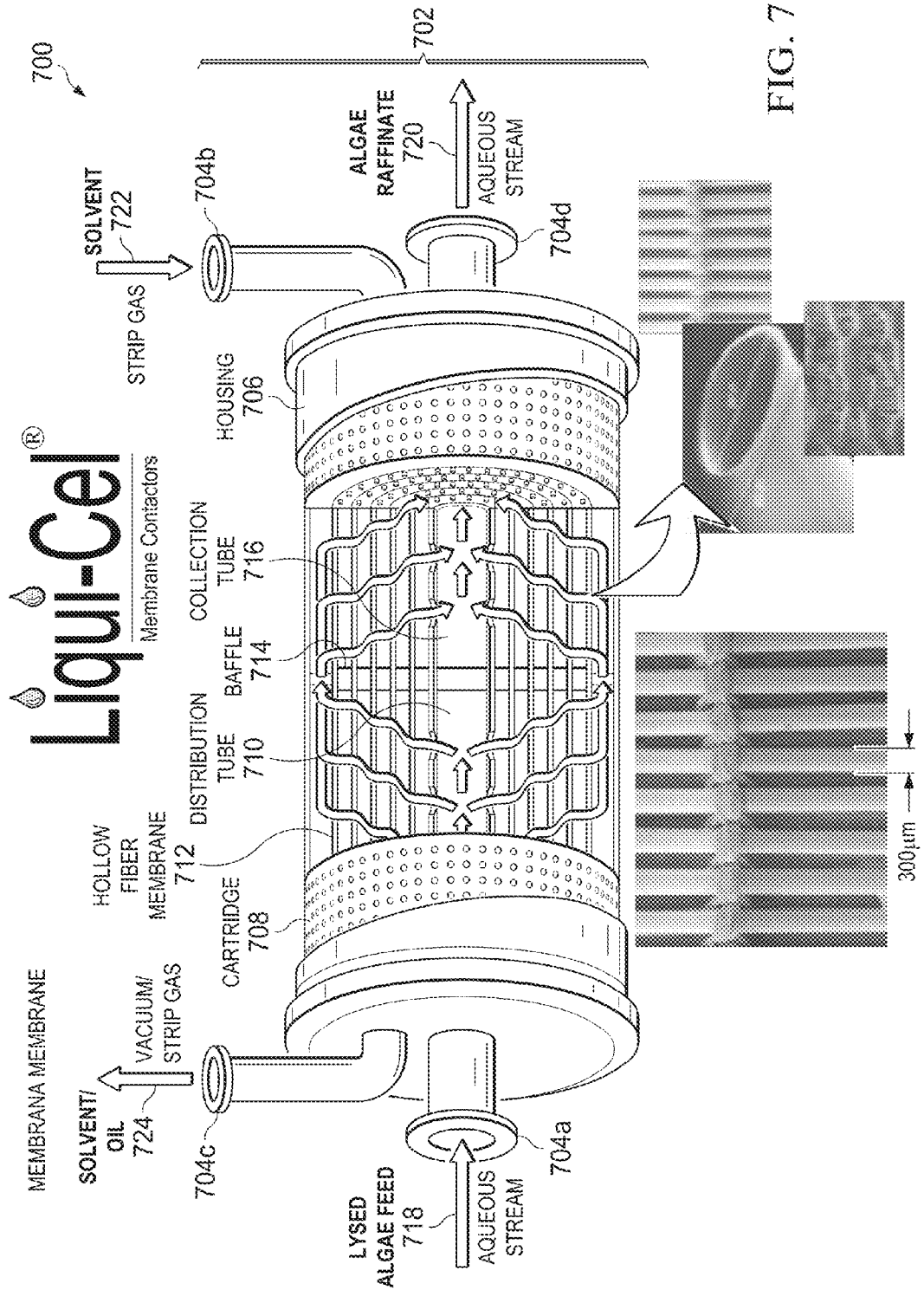
FIG. 7 is a schematic of the LIQUI-CEL™ extra flow microporous hollow fiber membrane contactor.

FIG. 7 is a schematic 700 of the Liqui-Cel extra flow microporous hollow fiber membrane contactor 702. The contactor 702 comprises a metallic or polypropylene housing 706, wherein is contained a cartridge 708 comprising a plurality of hydrophobic microporous hollow fibers 712, along with a distribution tube 710, a collection tube 716, and a central baffle 714. The housing 706 has 2 inlet ports (704a and 704b) and two outlet ports 704c and 704d.

As shown in FIG. 7, the aqueous phase 718 is fed through the port 704a on the shell-side while the solvent (or oil) phase 722 is fed on the fiber side through port 704b. The non-polar lipids coalesce onto the oil wetted hydrophobic surface of the fibers and dissolve into pores of the fiber walls and into the counterflowing collection fluid of the solvent (or oil) phase 722. A higher pressure is maintained on the aqueous side to prevent bleed through of the solvent (or oil) phase 722. However the shell-side pressure is kept below the pore breakthrough pressure which would force aqueous phase 718 into the solvent (or oil) phase 722. The algae concentrate 718 and collection fluid solvent feeds 722 could be operated at room temperature or preheated up to 60° C. The collection fluid solvent (or oil) phase 722 along with the recovered lipids or oils 724 is removed through outlet port 704c, and the aqueous algal raffinate containing the algal biomass and other solids 720 is removed through the port 704d.

While not intuitive because of the presence of Algae solids, the MHF contactor appears ideal for recovering oil from lysed Yeast. The MHF contactor provides: (i) high contact area for coalescence and mass transfer, (ii) processing of un-flocculated or deflocculated Algae solids, (iii) large flow capacities on the shell side, (iv) negligible mass transfer resistance in the pore because of the high equilibrium distribution coefficient of non-polar oils into non-polar solvent, and (v) low cost per unit of Algae flow per unit as the contact area is 100× that for the conventional liquid extraction contactor, (e.g. perforated plate column).

The MHF extractor provides four significant advantages: (i) no entrainment of solvent which eliminates the need for a stripping column when the proper solvent is selected, (ii) easy control of the liquid-liquid interface by controlling the pressures, (iii) extremely large area for coalescence of small Algae oil drops. The MHF contactor functions primarily as an oil coalescer. The solvent acts to simply remove the coalesced oils from the surface of the fibers, and (iv) while not optimized, commercial MHF contactor modules used for gas transfer are available and reasonably priced. The Liqui-Cel Extra Flow contactor is a good example.

MHF Contactor Performance Data: The present inventors characterize the performance of the MHF contactor for algae oil extraction. The objectives of the studies were to determine the fraction of non-polar algae extracted from the feed and determine if membrane plugging was observed. The 4-inch diameter Liqui-Cel Extra Flow Contactor, purchased from Membrana [Part#G503], was used to extract algae oil from an actual lysed algae concentrate (FIG. 7). Typical oil recoveries from experimentally lysed Algae ranged from 45-80% for a single module. The results of the studies are shown in Table 1. Differences in oil recoveries may be attributed to the lysing efficiency, polarity of the Algae oil, differences in oil wettability and coalescence onto the membrane fibers. Membrane plugging is not observed when processing lysed Algae concentrates where the Algae is not flocculated or has been deflocculated. Typical range of conditions associated with the recovery of non-polar Algae oil are shown in Table 1. These data are based on the processing of actual lysed Yeast. Since the non-polar oil recovery efficiency is also affected by the lysing efficiency, controlled experiments were carried out where known quantities of canola oil were injected into a re-circulating Algae concentrate stream. In the first set of studies, heptane was re-circulated on the tube side as a non-polar oil specific collection fluid. The results of these studies are shown in Table 2. In the initial small scale studies, 44-64% of the injected oil volume was recovered by the microporous hollow fiber membrane when only 25 mL's of canola oil was injected. When a larger quantity of canola oil was injected (250 mL), more than 90% of the injected oil volume was recovered as shown in Table 2. These data provide evidence that a fixed volume of oil is likely held up in the walls of the hollow fibers. In a second set of studies using canola oil injected into lysed algae concentrate, canola oil was re-circulated through the hollow fiber tubes as a collection fluid instead of heptane. As shown in Table 3, 93% of the 9 liters of injected canola oil was recovered, conclusively demonstrating that a "like" oil can be used as a collection fluid. The second set of studies validates the mechanism that the process is based on coalescing and recovery of the oil drops from the aqueous slurry can be done using a "like" oil. The canola oil runs also provide supporting data for the application of the non-dispersive microporous hollow fiber technology in removing residual oil from produced water, as canola oil/water emulsions are an accepted experimental proxy to mimic produced water in a laboratory setting. The results from Tables 2 and 3 indicate that oil recoveries approaching 100% are possible. The walls of the hollow fibers will always contain oil during processing.

TABLE 1

Typical algal oil recoveries from lysed algae with the MHF Contactor.

| Parameter | Overall Range | Typical Range |
|---|---|---|
| Algae concentration, wt % | 0.01-15 | 1-5 |
| Non-polar Oil in Algae, wt % | 0.5-10 | 2-6 |
| Algae Flow rate, gpm | 0.5-2 | 0.5-1 |
| Heptane Flow rate, gpm | 0.04-0.07 | 0.07 |
| Non-polar Oil Recovery, % | 40-90 | 70-80 |

TABLE 2

Results of controlled study using Heptane flowing through the tubes.

| Test | #1 | #2 | #3 | #4 |
|---|---|---|---|---|
| Oil Injected, ml | 25 | 25 | 210 | 210 |
| Oil Recovered, ml | 11 | 16 | 198 | 188 |
| Missing Oil | 114 | 99 | 12 | 22 |
| % Oil recovery | 44 | 66 | 94 | 90 |

Basis:
Algae feed rate = 1,000 lbs/hr,
Heptane feed rate = 50 lbs/hr,
Total mass of re-circulating algae = 50 lbs containing approximately 1.5 wt % bio-cellular solids,
Oil injection rate = 0.17 lbs/hr.

TABLE 3

Results of the solventless test with Canola oil flowing through the tubes. Shell-side and tube-side flows are re-circulated.

| | |
|---|---|
| Tube-Side | Canola Oil |
| Shell-Side | 50 lbs of Algae Concentrate |
| wt % bio-cellular solids in algae | Approximately 1.5 wt % |
| Tube Side Flow rate | 10-15 lbs/hr |
| Shell Side Flow rate | 500, lbs/hr |
| Canola Oil Injection Rate into Algae | 3 ml/min |
| Run Time | 72 hours |
| % Recovery of Injected Canola Oil | 93% |

It should be noted that the algae or Algae concentrate feed or bio-cellular feed must not contain flocculated algae or Algae or solids to prevent plugging within the membrane module. For the case of the MHF contactor described in the present invention, the minimum dimension for shell-side flow is 39 microns which greater than the size of most single alga. It is likely that flocculated algae or Algae will eventually plug the shell-side of the MHF contactor.

In a related and alternative process, the microporous membrane could be used to separate two liquids from a solid-liquid-liquid emulsion. The solid-liquid-liquid emulsion may have been derived from a process for recovering oil from a bio-cellular aqueous feed using a dispersive process. The microporous membrane hollow fiber contactor would allow the hydrocarbon liquid to "wet" and coalesce into the walls of the hollow fibers while preventing the hydrophilic solids or aqueous phase from entering. Thus the hydrocarbon liquid will exit the membrane on the tube side when an appropriate collection fluid is employed, while the aqueous liquid and solids will exit on the shell-side. An alternative process is shown in FIG. 9.

Figure 9:
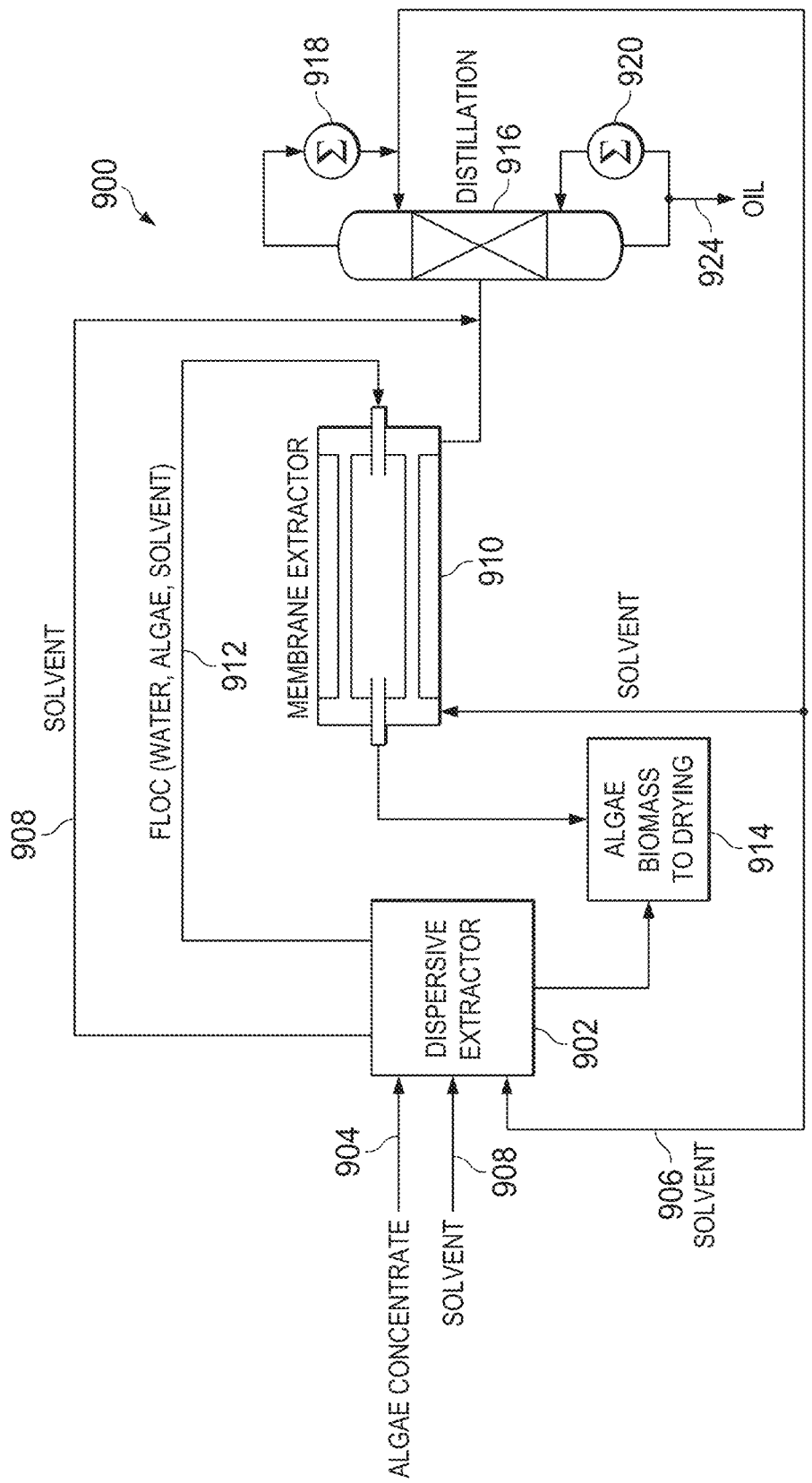
FIG. 9 shows an alternative process where a solid-liquid-liquid emulsion potentially derived from a dispersive extraction is fed to the shell-side of the microporous hollow fiber membrane for the purpose of separating the two liquids.

The flow diagram 900 shown in FIG. 9 of the alternative algae oil extraction process comprises a dispersive extraction column 902, lysed Yeast or algal concentrate 904 and solvent 908 is fed to a dispersive extractor such as a column extractor, centrifugal type extractor or mixer-settler 902. The solid-liquid-liquid emulsion (S-L-L) 912 from the column 902 comprising algae-water-solvent is then fed to a shell-side of a microporous membrane extractor (contactor) 910. Any solids (Yeast or algal biomass) from the column extractor 902 may be directly subjected to further processing (e.g. drying) as shown by step 914. The microporous membrane hollow fiber contactor 910 allows the hydrocarbon liquid to "wet" and coalesce into the walls of the hollow fibers while preventing the hydrophilic solids or aqueous phase from entering. The hydrocarbon liquid exits the membrane contactor 910 on the tube side when an appropriate collection fluid (for e.g. solvent 908) is employed on the tube side, while the aqueous liquid and solids (Yeast or algal biomass) will exit on the shell-side for further processing (e.g. drying) as shown by step 914. The hydrocarbon liquid is then fed to a distillation unit 916 (heat exchangers associated with the distillation unit are shown as 918 and 920) for removal of any residual solvent 906 and to recover the Yeast or algal oil 924. The recovered solvent 906 may be circulated back into the process, for e.g. as the collection fluid on the tube-side of the membrane contactor 910 or back to the dispersive extraction column 902.

The collection fluid on the tube side can be tailored to enhance recovery or selectively recover sub-sets of desired compounds, and leave others. Study data demonstrates that hydrocarbons and non-polar lipids are removed using heptane or like oil and phospholipids are not. Phospholipid recovery can likely be achieved by employing a more polar collection fluid.

Figure 8:
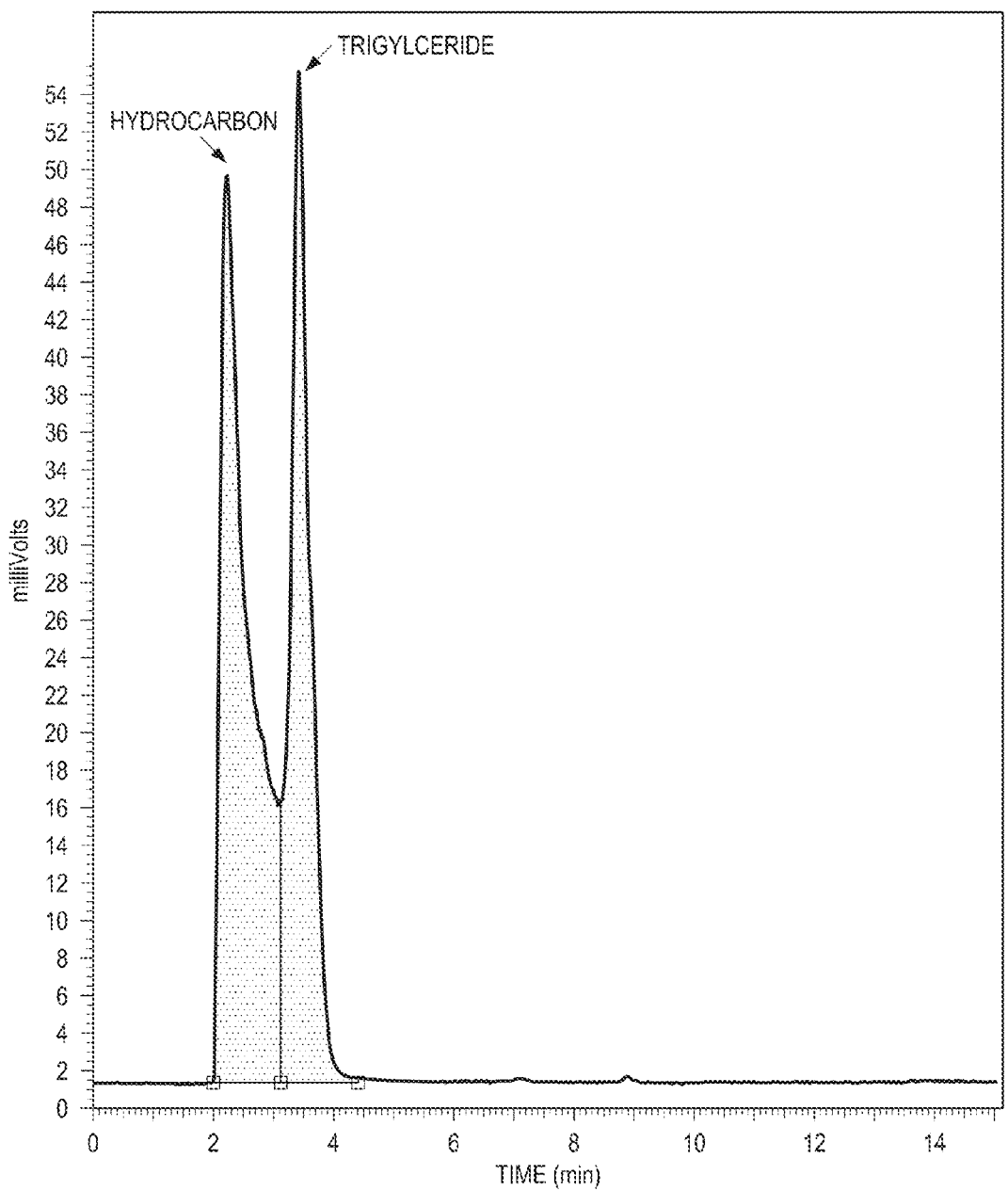
FIG. 8 is an HPLC trace (chromatogram) of oil obtained using hollow fiber membrane extraction of a lysed suspension of *Nanochloropsis*. Two main peaks are seen in this sample, the first is a mixture of various long chain hydrocarbons and the second is a triglyceride.

To determine the composition of the extracted oil, the inventors performed a normal phase HPLC using a Sedex 75 evaporative light scattering detector. As shown in FIG. 8, two main components were detected in this particular sample of oil, the first peak corresponding to long chain hydrocarbons and the second corresponding to triglycerides. In some samples, 1,3 and 1,2 diglyceride have also been detected.

Figure 10:
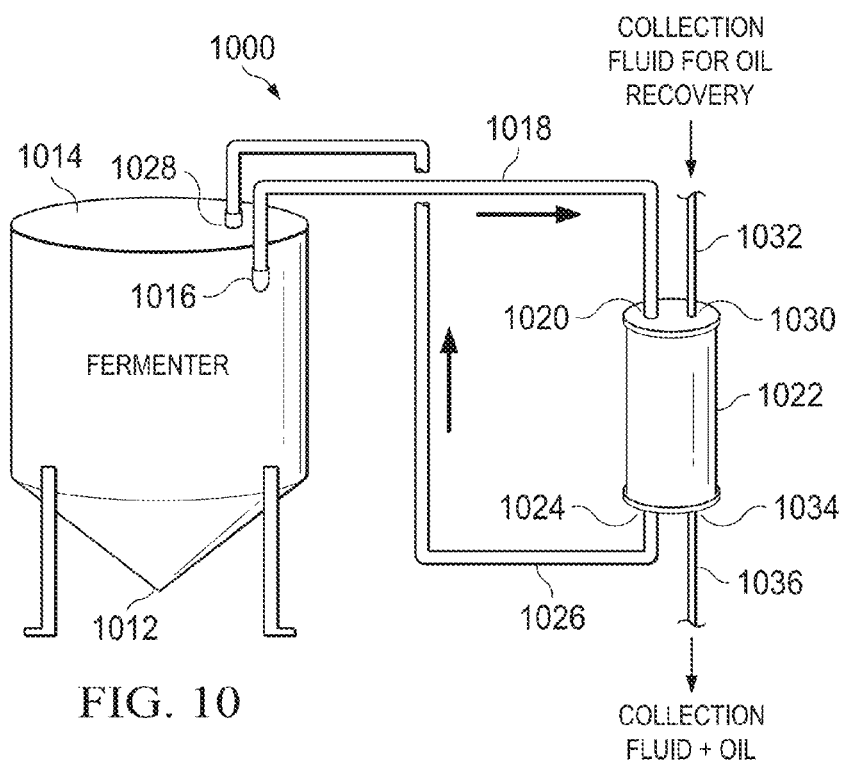
FIG. 10 shows a schematic representation of a fermenter coupled to a non-dispersive oil recovery module operating as a closed loop system.

The schematic representation in FIG. 10 shows a fermenter coupled to a non-dispersive oil recovery module operating as a closed loop system. The system 1000 comprises a fermenter 1012 containing the aqueous liquid source comprising organisms that produce oils or other hydrophobic substances (not depicted) that accumulate outside cells. The fermenter 1012 is optionally covered by a fermenter lid 1014. The liquid source exits the fermenter via the fermenter outflow valve 1016 and is transported via the contactor inflow pipe 1018 directly or indirectly to the contactor inflow valve 1020. In certain cases, the material may be pre-processed prior to entering the contactor (e.g., debris may be filtered or removed prior to entering the contactor). The liquid source enters the non-dispersive membrane contactor 1022 and exits the contactor 1022 via the contactor outflow valve 1024. The liquid source, in part or whole, is further transported via the fermenter inflow pipe 1026 to the fermenter inflow valve 1028 and circulated back into the fermenter 1012. In some cases, some of the growth media volume and/or cells may be removed from the stream to allow additional nutrients to be added. Collection fluid (not depicted) is fed or pumped via the collection fluid inflow pipe 1032, and the collection fluid inflow valve 1030 into the contactor 1022. The collection fluid counterflows with the liquid source in the contactor 1022 and exits the contactor via the collection fluid outflow valve 1034 into the collection fluid outflow pipe 1036.

Figure 11:
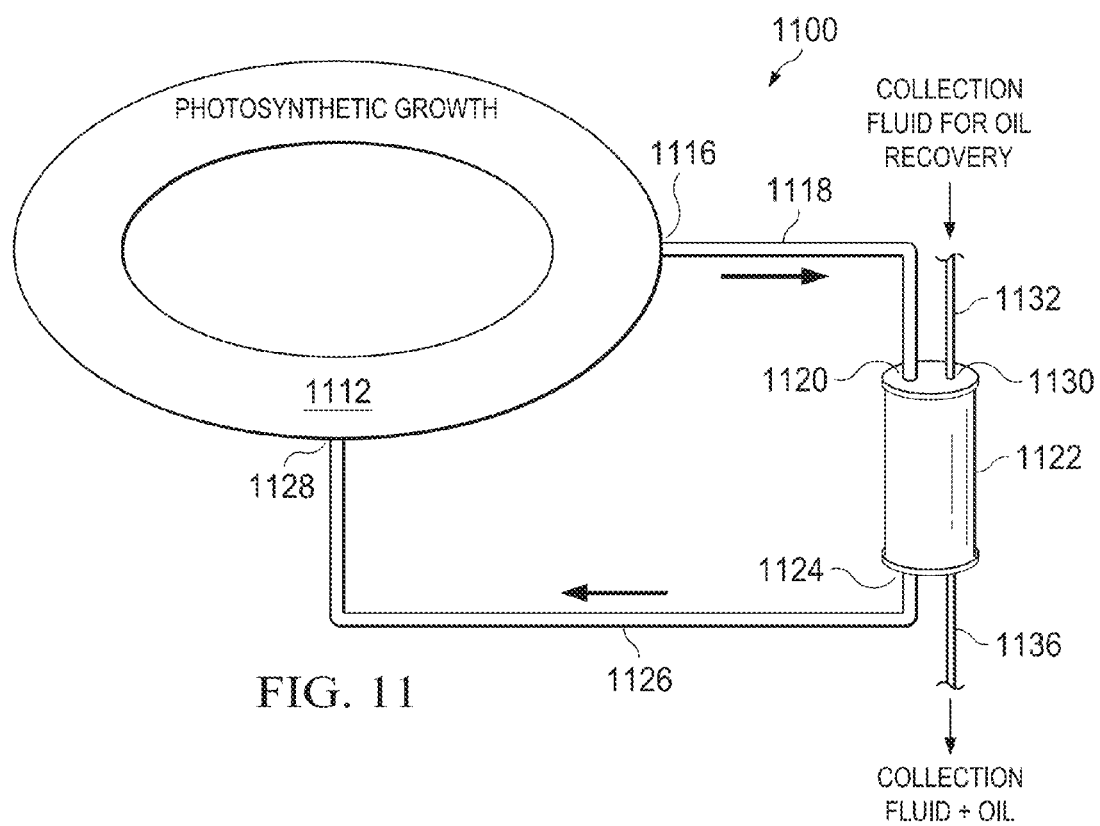
FIG. 11 is a schematic representation of a photobioreactor coupled to a non-dispersive oil recovery module operating as a closed loop system.

The schematic representation in FIG. 11 shows a schematic representation of a photobioreactor or closed or open pond coupled to a non-dispersive oil recovery module operating as a closed loop system. The system 1100 comprises a photobioreactor or pond 1112, where photosynthetic growth occurs and which is designed to contain an aqueous liquid source comprising organisms that are capable of photosynthesis and capable of secreting oils or other hydrophobic substances (not depicted). Many forms of photosynthesis are suitable in the system 1100, but generally utilize $CO_2$ or $HCO_3$ and light. The liquid source exits the photobioreactor 1112 via the photobioreactor outflow valve 1116 and is transported via the contactor inflow pipe 1118 directly or indirectly to the contactor inflow valve 1120. The liquid source enters the non-dispersive membrane contactor 1122 and exits the contactor 1122 via the contactor outflow valve 1124. The liquid source is further transported via the photobioreactor inflow pipe 1126 to the photobioreactor inflow valve 1128 and circulated back into the photobioreactor or pond 1112. Collection fluid (not depicted) is fed or pumped via the collection fluid inflow pipe 1132 and a collection fluid inflow valve (not depicted) into the contactor 1122. The collection fluid counterflows with the liquid source in the contactor and exits the contactor 1122 via the collection fluid outflow valve (not depicted) and the collection fluid outflow pipe 1136.

FIGS. 12A and 12B shows the creation, visualization and separation of an algae/water/ISOPAR™ V (ExxonMobil) emulsion. FIG. 12A is a representative light micrograph of the *Chlorella*/water/ISOPAR™ V mixture stained with Oil Red O. FIG. 12B is a representative light micrograph of the *Chlorella*/water/ISOPAR™ V mixture stained with Oil Red O after passing through the oil recovery membrane once. Droplets of ISOPAR™ V stain red. *Chlorella* sp. was grown in F/2 medium under artificial lighting. 10 L of culture (~0.45 mg/L algae) were removed to a separate vessel. 1 L of ISOPAR™ V, a model fungible diesel hydrocarbon, was vigorously integrated into the algae by constant mixing; oil was visualized by Oil Red O staining and light microscopy.

FIG. 13 shows removal of ISOPAR™ V with a single pass through the membrane. ISOPAR™ V collected from 50 mL aliquots (in triplicate) of the emulsion prior to and after passing through the membrane was weighed to assess oil removal (a sample of algae without ISOPAR™ V added is shown for reference). Using the present invention it was found that a 98% of the oil was removed from the emulsion was collected by the membrane and could be recovered. A microporous hollow fiber membrane was pre-primed with ISOPAR™ V. The mixture of ISOPAR™ V/water/algae was passed through the membrane at a rate of 1 gpm to evaluate oil removal.

Figure 14:
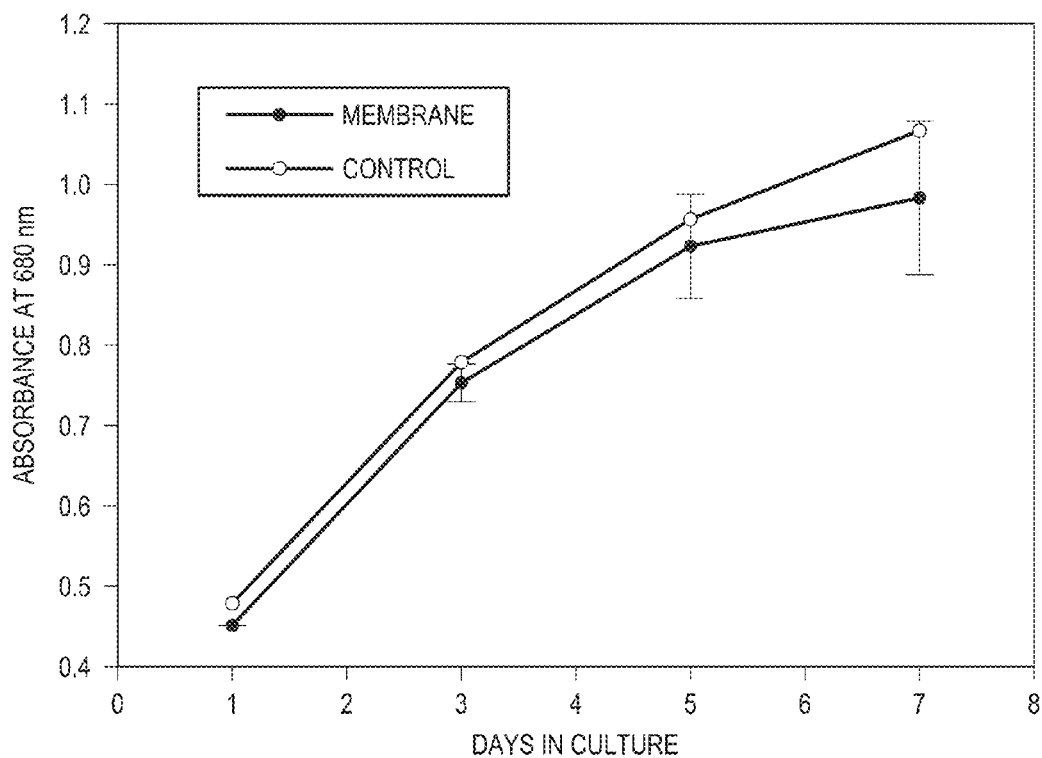
FIG. 14 shows regrowth of *Chlorella* sp. following a single pass through the membrane.

FIG. 14 demonstrates regrowth of *Chlorella* sp. following a single pass through the membrane. 50 mL aliquots (in triplicate) were regrown following a single pass through the membrane, with no supplemental nutrients added. Untreated samples of *Chlorella* from the same source were grown in parallel for comparison. Oil in the emulsion before and after passing through the membrane was recovered using hexane and weighed. Untreated aliquots of *Chlorella* sp. and those that passed through the membrane were regrown to assess impacts on cell health.

Figure 15:
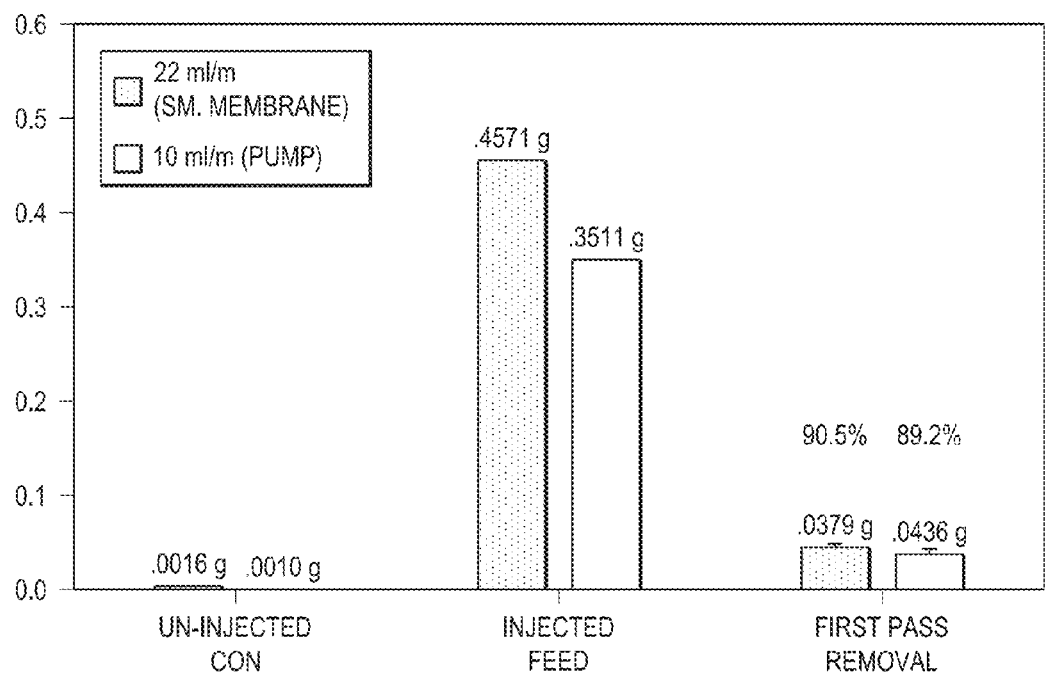
FIG. 15 is a graph that demonstrates the removal with a single pass through the membrane.

FIG. 15 is a graph that demonstrates the removal with a single pass through the membrane. The graph illustrates the removal amount with a 22 ml/m Sm. Membrane and a 10 ml/m pump being used and shows a 90.5% and a 89.2% removal with a first pass compared to the injected feed.

Figure 16:
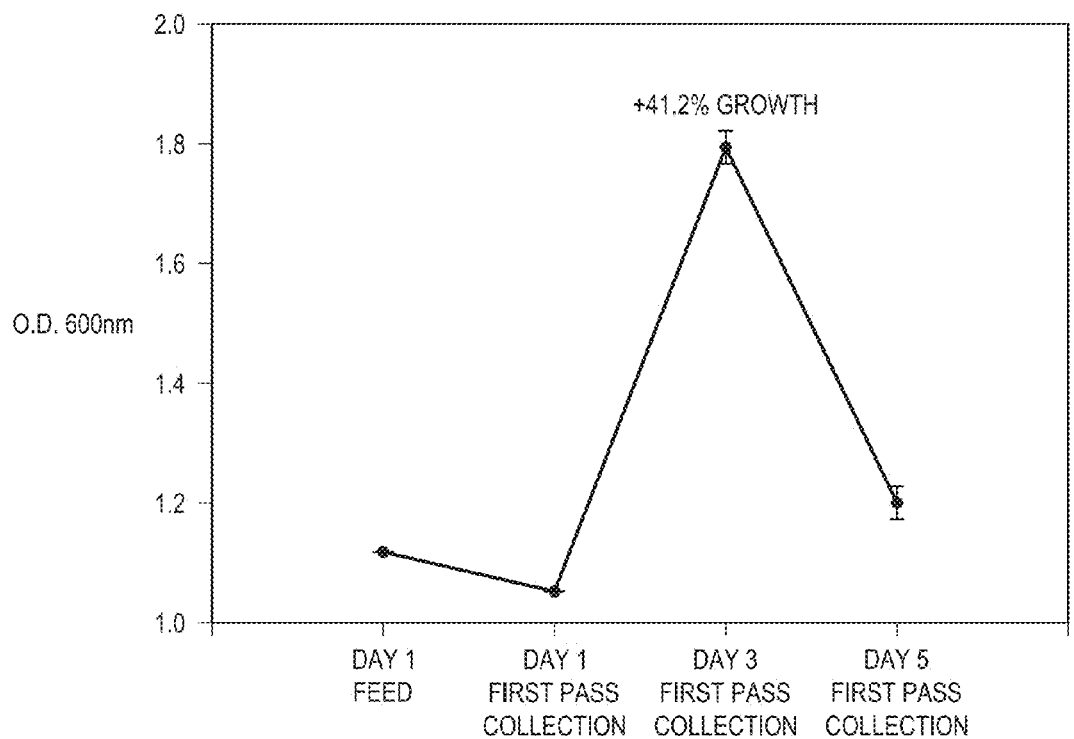
FIG. 16 shows regrowth following a single pass through the membrane.

FIG. 16 shows regrowth following a single pass through the membrane looking at the optical density of the culture (e.g., absorbance at 600 nm) at 1, 3 and 5 days past the 1st collection. The Yeast were passed through the membrane one time, then placed back into culture. There was a slight decrease in Yeast density following passage through the membrane, suggesting that a small amount of yeast remained in the system (e.g., in membrane or filter traps). However, the Yeast that were put back into culture nearly doubled in density, then began to perish, likely due to contamination (yeast cells were not suspended in culture, but accumulated on the bottom of the tub).

Figure 17:
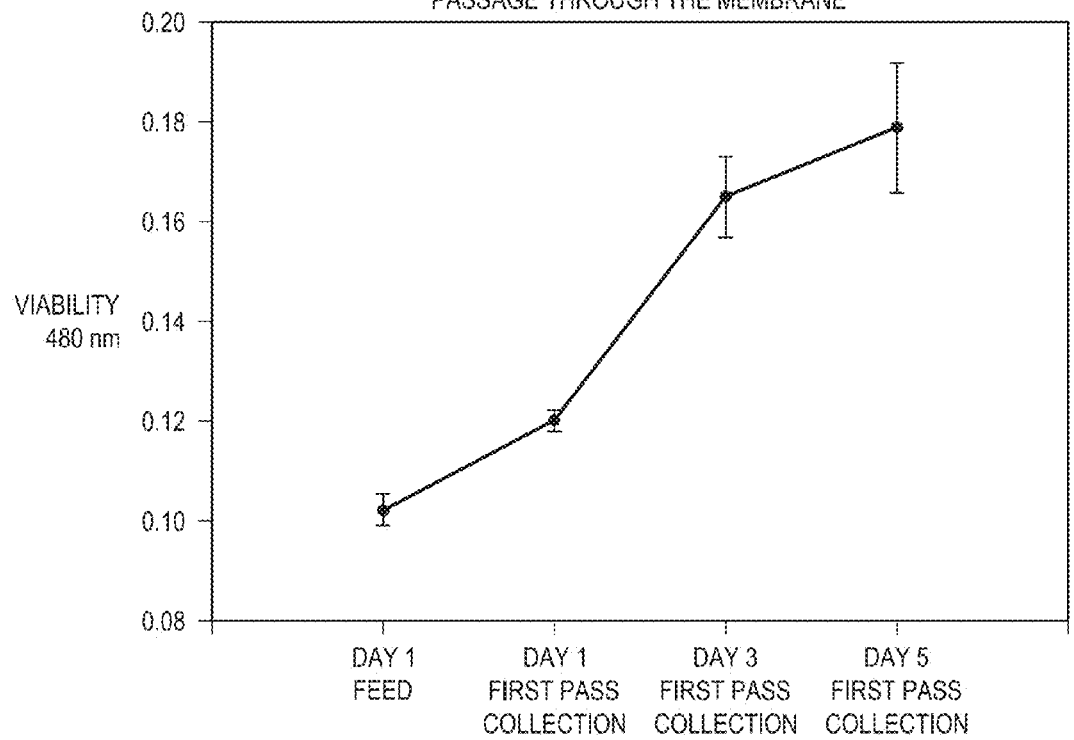
FIG. 17 is a plot that shows Yeast regrowth following passage through the membrane.

FIG. 17 is a plot that shows Yeast regrowth following passage through the membrane. The viability of the culture continued to increase for at least 5 days following passage through the membrane. The O.D. 600 readings at day 5 indicated a drop in yeast density, while the viability of the culture continues to increase at day 5. The yeast cells did not remain suspended in culture, and therefore may not have been accurately measured by the spectrophotometer. This suggests that either the yeast cells were viable, but collected at the bottom of the tube, or that the yeast cells were non-viable and that a bacterial component accounted for the increase in viability, but did not have the equivalent absorbance capability as the yeast cells.

Figure 18A:
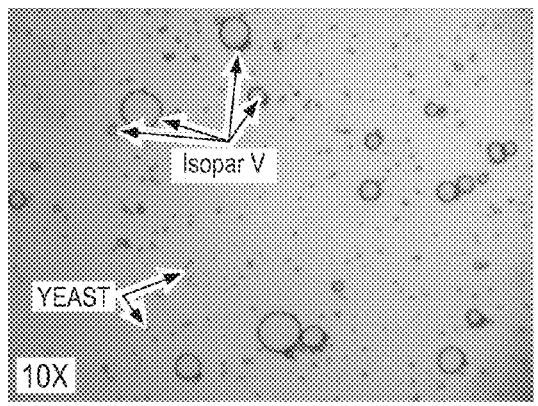
FIGS. 18A-18D shows the creation, visualization and separation of a Yeast/water/ISOPAR™ V emulsion.
Figure 18B:
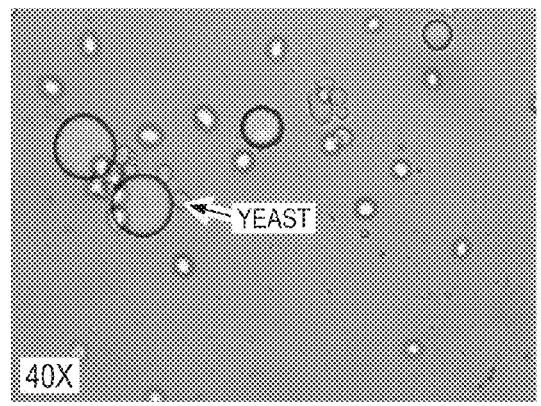
Figure 18C:
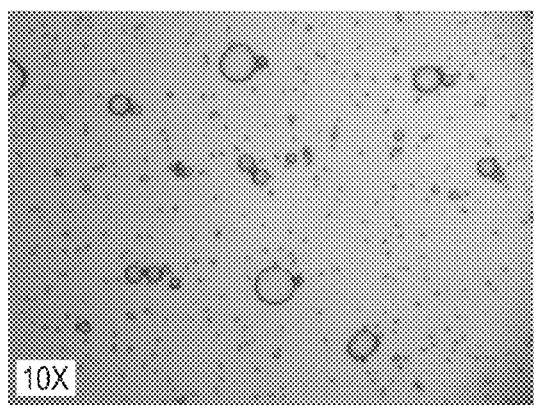
Figure 18D:
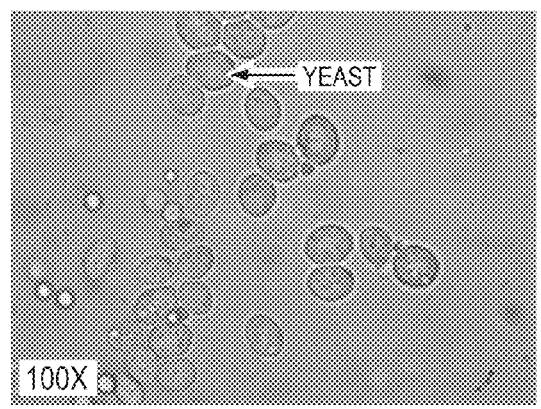

FIGS. 18A-18D shows the creation, visualization and separation of a Yeast/water/ISOPAR™ V (ExxonMobil) emulsion at initial injection feed. FIGS. 18A and 18B are representative light micrograph of the Yeast/water/ISOPAR™ V mixture. FIGS. 18C and 18D are images showing the relative size of the Yeast and ISOPAR™ V droplets.

Figure 19A:
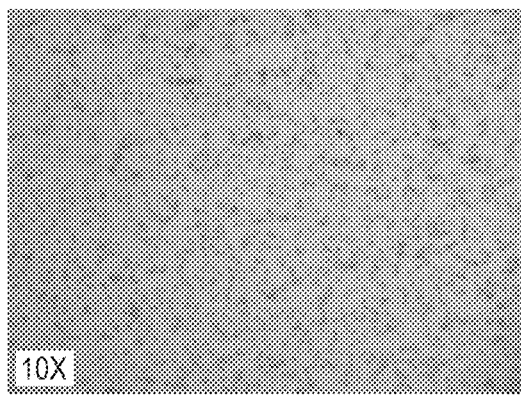
FIGS. 19A-19D shows the creation, visualization and separation of a Yeast/water/ISOPAR™ V emulsion following one pass through the membrane.
Figure 19B:
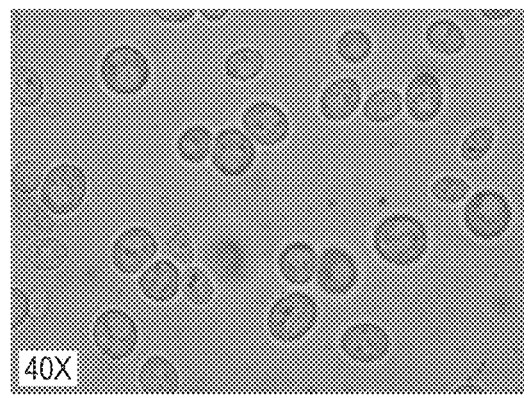
Figure 19C:
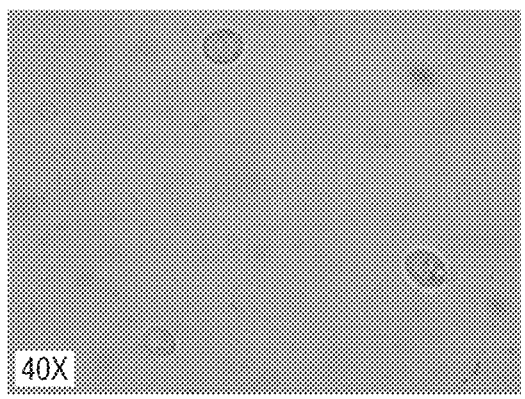
Figure 19D:
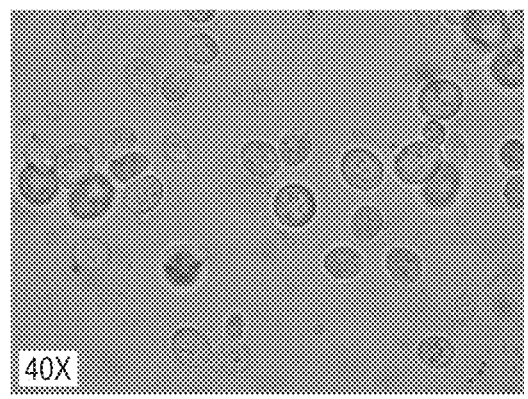

FIGS. 19A-19D shows the creation, visualization and separation of a Yeast/water/ISOPAR™ V (ExxonMobil) emulsion after first pass. FIGS. 19A and 19B are representative light micrograph of the Yeast/water/ISOPAR™ V mixture. FIGS. 19C and 19D are images showing the relative size of the Yeast and ISOPAR™ V droplets. As seen following 1 pass through the membrane, large Isopar droplets are removed while submicron sized droplets remain

TABLE 4

Results of the test with ISOPAR V flowing through the tubes with shell-side and tube-side flows re-circulated.

| | |
|---|---|
| Tube-Side | ISOPAR V |
| Shell-Side | Yeast |
| Injection of ISOPAR V | Approximately 3.4 L |
| Recovery of ISOPAR V | Approximately 3.35 L |
| Tube Side Flow rate | 0.02 gpm |
| Shell Side Flow rate | 0.5 gpm |
| Injection Rate | 10 ml/min |
| % Recovery of Injected ISOPAR V | 98.5% |

The inventors recognize that a host of strategies can be explored to develop biocatalysts that can convert carbon inputs into renewable oils. The inventors recognize that designer organisms that produce and secrete fungible oils may advance out of the lab and into pilot scale production, and the various biotech-based platforms already make oils at prices that can compete in established niche markets. A platform based on a designer or natural organism, which can convert a carbon source to oil and accumulate it outside the live cell, will ideally be able to recover the oil without harming the organism. Designer organisms can be produced that accumulate oil outside cells and may also be capable of photosynthesis; the organism may keep growing and the oil is actively recovered.

The inventors have developed a new concept in oil recovery that achieves oil coalescence in the presence of Yeast or algal cells. The technique is remarkably efficient and inexpensive and relies on commercially available, highly-scalable, membrane technology. In this regard, FIGS. 12 and 13 demonstrate that an experimental insoluble oil/water/algae emulsion can be separated into insoluble oil and water/algae fractions with a single pass through the oil recovery membrane process. FIG. 14 demonstrates that a single pass through the membrane will not materially impact the viability of the cells and/or the production of insoluble oils by the Yeast.

The oil recovery technique is used to recover oils from aqueous slurries, e.g., lysed Yeast cells, non-lysed Yeast cells, or lysed, non-lysed and/or partially lysed microorganisms such as bacteria, yeast, or other single or small multi-cell organisms. The present invention provides a robust oil/water/algae or Yeast separation technique for, e.g., biocatalyst platforms. The results show that (1) an emulsion can be efficiently removed from the Yeast or algal stream using the membrane technology; (2) the efficiency of oil removal is excellent with >95% of the oil is removed after a single pass despite the presence of cells; (3) passing through the membrane does not inhibit future cell growth. These studies and results and disclosure demonstrate that fungible, drop-in hydrocarbon molecules can be easily and rapidly recovered from water and away from Yeast using the invention. These studies also demonstrate the feasibility of the recovery of oil accumulated outside live organisms, whereby the organism does not have to be lysed and are not harmed during the oil recovery process. A bio-catalyst platform that makes micron-sized oil droplets could use this inexpensive, scalable and proven technique to recover oil and keep the designer microbe alive to produce additional product.

These studies also support recovery of different hydrophobic or oil-soluble products (i.e., TAG); removal of oil from higher stability emulsions with smaller oil droplets; and that the technique can be applied to non-Yeast biocatalyst platforms making drop-in hydrocarbon molecules. These hydrocarbons could be isolated with an efficiency of 90, 91, 92, 93, 94, 85, 96, 97, 98, and 99% efficiency using the present invention.

One embodiment of the system includes coupling of the non-dispersive membrane contactor to growth environments in a closed loop fashion, as shown in FIGS. 10 and 11. The non-dispersive membrane contactor can be operated as a flow-through device, continuously collecting oil from aqueous slurries passing through the module. The inventors recognize that certain growth environments, such as fermenters or photobioreactors or pond are ideally operated in a clean fashion to minimize contamination and growth of unwanted organisms. The membrane contactor can be operated in conjunction with growth environments requiring clean operating conditions by connecting the in-flow and out-flow valves of the contactor with the growth chamber (via piping). Operated in this fashion, the growth media could circulate through the membrane contactor and emerge de-oiled and uncontaminated from the out-flow valve, allowing both the cells and growth media to be re-circulated into the growing environment, while the oil is collected in the module.

The oil recovery module is an extension of the growth environment, and the flow rate may be measured in liters or gallons per minute. The residence time in the module is very short, so the oil recovery step only has minimal effect on the viability of the cells or the temperature of the media. This mode of operation drastically increases the cost efficiency of the bio-hydrocarbon production by enabling continuous growth and continuous oil recovery and minimizing reactor downtime. Constantly removing the accumulating hydrocarbon may prompt the synthesis of additional hydrocarbon (by removing end-product inhibition, for example), depending on how the underlying metabolic pathways are regulated (Le Chatlier's principle).

One advantage of the present invention is the development of a non-lethal recovery system, which further reduces operating expenses for biohydrocarbon production by increasing yields per cell. It also increases operating efficiency by recovering oil in relatively smaller, continuous and predictable quantities. It may decrease expenses by enabling longer runs with less operational hours spent on cleaning and re-starting cultures. For photosynthetic organisms, the presence of oil in the growth media or adhering to cells may obscure light, reducing the efficiency of photosynthesis; active removal of this oil would be expected to increase the net photosynthesis.

It will be understood by the skilled artisan that the process described hereinabove is applicable broadly for insoluble oil recovery beyond yeast, E. coli, etc., mixed cultures of cells, grown by any method (not limited to photosynthetic organisms), aqueous slurries containing broken and/or live cells or no cells (in case pre-treated to remove cells/cell debris or other suspended materials). The process can also be used to recover oil from any liquid source comprising insoluble oils for e.g. industrial water, brine, wastewater, industrial or natural effluents, water-oil mixtures, aqueous slurries, aqueous slurries comprising broken cells, live cells or combinations thereof, bio-cellular mixtures, lysed cellular preparations, and combinations thereof. The process of the present invention is capable of extracting almost up to a 100% of the one or more insoluble oils in the liquid source. The process provides insoluble oil recoveries of 45%, 50%, 55%, 60%, 65%, 70%, 75%, 80%, 85%, 90%, 95%, 98%, 99% and 100% from the liquid source.

The method and the process of the present invention can be expanded for recovery of a variety of molecules depending upon choice of collection fluid and to include single or multi-step, differential recovery processes for e.g., specifically recover non-polar oil with one membrane module, then treat the effluent with a second membrane module employing a different collection fluid. The collection fluids may be selective, partially selective or non-selective for specific compounds. In other specific examples, the present invention may be used to specifically recover non-polar oil with one membrane module, then followed by treatment of the effluent from the first module with a second membrane module employing a different collection fluid.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 4,439,629: Extraction Process for Beta-Carotene.
U.S. Pat. No. 5,378,639: Solvent Extraction.

What is claimed is:

1. A method of extracting one or more insoluble oils from a liquid source that comprises insoluble oils and yeast, comprising using one or more membrane contactors, comprising the steps of:
   pumping the liquid source comprising the one or more oils and yeast from a reactor to the one or more membrane contactors wherein the liquid source does not contain a dispersing agent;
   coalescing the one or insoluble oils within the liquid source onto a first surface of the one or more membrane contactors;
   pumping a collection fluid through the one or more membrane contactors on a second surface of the one or more membrane contactors;
   contacting the one or more coalesced oils in the liquid source with the collection fluid pumped in the one or more membrane contactors;
   pumping a first stream from the one or more membrane contactors back to the reactor, wherein the first stream comprises the liquid source with the yeast without extracted oils, wherein the yeast remain viable; and
   removing a second stream from the one or more membrane contactors, wherein the second stream comprises the collection fluid and extracted oils.

2. The method of claim 1, wherein the yeast comprise intact yeast cells, lysed yeast cells or a combination of both.

3. The method of claim 1, further comprising the step of separating the yeast cells from the liquid source.

4. The method of claim 1, further comprising the step of lysing the yeast cells in the liquid source.

5. The method of claim 1, wherein the reactor is a fermenter, and the yeast are capable of secreting oil.

6. The method of claim 1, wherein the yeast are selected from *Cryptococcus curvatus, Cryptococcus terricolus, Lipomyces starkeyi, Lipomyces lipofer, Endomycopsis vernalis, Rhodotorula glutinis, Rhodotorula gracilis, Candida* 107, *Saccharomyces paradoxus, Saccharomyces mikatae, Saccharomyces bayanus, Saccharomyces cerevisiae,* any *Cryptococcus, C. neoformans, C. bogoriensis, Yarrowia lipolytica, Apiotrichum curvatum, T. bombicola, T apicola, T. petrophilum, C. tropicalis, C. lipolytica,* and *Candida* sp.

7. The method of claim 1, wherein the yeast is capable of secreting oil or causing the accumulation of oil outside living cells.

8. The method of claim 1, further comprising contacting the yeast with chemical probes, exogenous agents, or pharmaceuticals, whereby the metabolism of the one or more yeast is modified, wherein at least one yeast causes accumulation of the one or more oils outside living cells.

9. The method of claim 1, wherein contacting the one or more oils in the liquid source with the collection fluid allows the yeast to continue to produce the insoluble oils.

10. The method of claim 1, wherein the liquid source is selected from the group consisting of industrial water, brine, wastewater, industrial or natural effluents, water-oil mixtures, aqueous slurries, aqueous slurries comprising broken cells, live cells, biocellular mixtures, lysed cellular preparations, or combinations thereof.

11. The method of claim 1 wherein the yeast are genetically modified to render them capable of secreting one or more insoluble oils and are capable of causing accumulation of the one or more insoluble oils outside yeast living cells upon induction with one or more chemical probes, exogenous agents, pharmaceuticals, or combinations thereof.

12. The method of claim 1, wherein between 95 and 100% of the one or more insoluble oils in the liquid source are extracted.

13. The method of claim 1, wherein 45%, 50%, 55%, 60%, 65%, 70%, 75%, 80%, 85%, 90%, 95%, 98%, 99% or 100% of the one or more insoluble oils in the liquid source are extracted.

14. The method of claim 1, wherein the collection fluid comprises one or more solvents, a biodiesel, an oil, an algal oil, a yeast oil, a non-polar oil or mixtures, the oil secreted by the yeast, or combinations thereof.

15. A method of extracting one or more insoluble oils or hydrophobic components from a growth media comprising yeast and the insoluble oils using one or more hydrophobic membrane contactors comprising the steps of:
   pumping the growth media comprising the yeast and insoluble oils from a reactor into the one or more hydrophobic membrane contactors wherein the growth media does not contain a dispersing solvent;
   pumping one or more collection fluids through the one or more hydrophobic membrane contactors, wherein the one or more collection fluids counterflow with the growth media comprising yeast in the hydrophobic membrane contactor;
   coalescing the insoluble oils or hydrophobic components within the growth media onto a first surface of the one or more hydrophobic membrane contactors;
   contacting the coalesced insoluble oils or hydrophobic components within the growth media comprising yeast and insoluble oils in the hydrophobic membrane contactor with one or more collection fluids pumped through the one or more hydrophobic membrane contactors on a second surface of the one or more hydrophobic membrane contactors;

removing a first stream from the one or more hydrophobic membrane contactors wherein the first stream comprises the growth media and yeast, wherein the yeast do not exhibit reduced growth or reduced viability; and removing a second stream from the one or more hydrophobic membrane contactors wherein the second stream comprises the one or more collection fluids and the one or more insoluble oils.

16. The method of claim 15, further comprising feeding or pumping the first stream to the reactor to resume production by the yeast.

17. The method of claim 15, wherein the hydrophobic membrane of the hydrophobic membrane contactor comprises polyethylene, polypropylene, polyolefins, polyvinyl chloride (PVC), amorphous Polyethylene terephthalate (PET), polyolefin copolymers, poly(etheretherketone) type polymers, surface modified polymers, mixtures or combinations thereof.

18. The method of claim 15, wherein the counterflowing collection fluid comprises non-polar solvents, alkanes, aromatic solvents, ethers, halogenated solvents, or esters.

19. The method of claim 15, wherein the counterflowing collection fluid comprises hexane, benzene, toluene, diethyl ether, chloroform, dichloromethane, or ethyl acetate.

20. The method of claim 15, wherein the counterflowing collection fluid comprises one or more solvents, a biodiesel, an oil, an algal oil, a yeast oil, a non-polar oil or mixtures, the oil secreted by the yeast, or combinations thereof.

21. The method of claim 15, wherein the reactor is a fermenter, and the yeast is capable of secreting one or more insoluble oils.

22. The method of claim 15, wherein the yeast causes accumulation of one or more insoluble oils outside living cells.

23. The method of claim 15, further comprising contacting the yeast with chemical probes, exogenous agents, or pharmaceuticals, whereby the metabolism of the yeast is modified to causes accumulation of the one or more insoluble oils outside living cells.

24. The method of claim 15, wherein the step of contacting the growth media comprising yeast in the one or more hydrophobic membrane contactors with one or more collection fluids pumped through the one or more hydrophobic membrane contactors and the yeast continue to produce insoluble oils.

25. The method of claim 15, wherein the yeast are genetically modified to render them capable of secreting one or more hydrophobic components, and are capable of causing accumulation of the one or more hydrophobic components outside yeast living cells upon induction with one or more chemical probes, exogenous agents, pharmaceuticals, or combinations thereof.

26. The method of claim 15, wherein at least 45%, 50%, 55%, 60%, 65%, 70%, 75%, 80%, 85%, 90%, 95%, 98%, 99% or 100% of the one or more insoluble oils in the growth media are extracted.

27. The method of claim 15, wherein the collection fluid comprises one or more solvents, a biodiesel, an algal oil, a non-polar oil or mixtures, the oil secreted by the yeast, or combinations thereof.

* * * * *